(12) United States Patent
Ali et al.

(10) Patent No.: US 11,571,155 B2
(45) Date of Patent: Feb. 7, 2023

(54) SYSTEM AND METHOD FOR COMPLETING A MEASUREMENT OF ANXIETY

(71) Applicant: Honda Motor Co., Ltd., Tokyo (JP)

(72) Inventors: Zainab I. Ali, Marysville, OH (US); Patricia A. Scott, Galloway, OH (US); Asimina Kiourti, Columbus, OH (US); Bofei Zhang, Jersey City, NJ (US); James Ciotola, Cuyahoga Falls, OH (US); Joel Pepper, Columbus, OH (US); August Mason, Baltimore, MD (US); Dhiren Bavisi, Kuala Lumpur (MY); Anna Lee, South Lyon, MI (US); Sean Duann, Jackson, TN (US)

(73) Assignee: HONDA MOTOR CO., LTD., Tokyo (JP)

( * ) Notice: Subject to any disclaimer, the term of this patent is extended or adjusted under 35 U.S.C. 154(b) by 894 days.

(21) Appl. No.: 16/434,137

(22) Filed: Jun. 6, 2019

(65) Prior Publication Data
US 2020/0383622 A1 Dec. 10, 2020

(51) Int. Cl.
*A61B 5/00* (2006.01)
*A61B 5/16* (2006.01)
*A61B 5/18* (2006.01)
*A61B 5/11* (2006.01)
*A61B 5/08* (2006.01)
*G06N 3/08* (2023.01)
(Continued)

(52) U.S. Cl.
CPC ............ *A61B 5/165* (2013.01); *A61B 5/0816* (2013.01); *A61B 5/1101* (2013.01); *A61B 5/113* (2013.01); *A61B 5/18* (2013.01); *A61B 5/6893* (2013.01); *A61B 5/721* (2013.01); *A61B 5/7267* (2013.01); *G06N 3/08* (2013.01); *A61B 2562/0247* (2013.01); *A61B 2562/0261* (2013.01); *A61B 2562/046* (2013.01); *G06N 3/04* (2013.01); *G06N 3/0445* (2013.01)

(58) Field of Classification Search
CPC ..... A61B 5/165; A61B 5/0816; A61B 5/1101; A61B 5/113; A61B 5/18; A61B 5/6893; A61B 5/721; A61B 5/7267; A61B 5/7264; A61B 2562/0247; A61B 2562/0261; A61B 5/168; G06N 3/08
See application file for complete search history.

(56) References Cited

U.S. PATENT DOCUMENTS

| | | |
|---|---|---|
| 5,835,008 A | 11/1998 | Colemere, Jr. |
| 6,575,902 B1 * | 6/2003 | Burton ................... G08B 21/06 600/595 |
| 8,872,640 B2 | 10/2014 | Horseman |

(Continued)

*Primary Examiner* — Scott M. Getzow
(74) *Attorney, Agent, or Firm* — Rankin, Hill & Clark LLP

(57) ABSTRACT

A system and method for determining a measurement of anxiety in a vehicle that include receiving sensor data from a plurality of sensors disposed within a plurality of areas of the vehicle. The system and method also include processing the sensor data into metrics associated with a type of measurement. Processing of the sensor data is completed by a neural network. The system and method also include analyzing the processed metrics and determining an anxiety level associated with an occupant of the vehicle. The system and method further include training the neural network based on the anxiety level and at least one driving event that is correlated with the anxiety level.

20 Claims, 6 Drawing Sheets

(51) Int. Cl.
*A61B 5/113* (2006.01)
*G06N 3/04* (2023.01)

(56) References Cited

U.S. PATENT DOCUMENTS

| | | |
|---|---|---|
| 9,165,280 B2 | 10/2015 | Basson et al. |
| 9,848,814 B2 | 12/2017 | Benson et al. |
| 2015/0229341 A1 | 8/2015 | Fung et al. |
| 2016/0157783 A1 | 6/2016 | Fung et al. |
| 2017/0161576 A1 | 6/2017 | Banno et al. |
| 2017/0313319 A1 | 11/2017 | Kishi et al. |
| 2019/0049267 A1* | 2/2019 | Huang ................ G01C 21/3415 |
| 2019/0184853 A1* | 6/2019 | Thomas ............ B60R 21/01516 |
| 2019/0282178 A1* | 9/2019 | Volosin ................ A61B 5/1102 |

* cited by examiner

SYSTEM AND METHOD FOR COMPLETING A MEASUREMENT OF ANXIETY

BACKGROUND

Currently measuring biometric parameters of vehicle occupants may involve the use of various cameras that may be located within various areas of a vehicle. Such cameras may be utilized to record occupant activity within the vehicle. Accordingly, occupants may find the utilization of such cameras as overly intrusive. Additionally, sensors have been used that may be attached to the occupant through wearable devices that may sense biometrics. However, such sensors may also be perceived to be intrusive and may require the occupant to continually wear the wearable devices to determine biometrics. Moreover, the data provided by the wearable sensors may be susceptible to various levels of noise caused by road vibrations, individual movement, vehicle movement, inertial movement, etc. The combination of such noise and the various types of data that may be provided by the cameras and sensors of the wearable devices may result in skewed/altered measurements of occupant biometric characteristics.

BRIEF DESCRIPTION

According to one aspect, a computer-implemented method for determining a measurement of anxiety in a vehicle that includes receiving sensor data from a plurality of sensors disposed within a plurality of areas of the vehicle. The computer-implemented method also includes processing the sensor data into metrics associated with a type of measurement. Processing of the sensor data is completed by a neural network. The computer-implemented method additionally includes analyzing the processed metrics and determining an anxiety level associated with an occupant of the vehicle. The computer-implemented method further includes training the neural network based on the anxiety level and at least one driving event that is correlated with the anxiety level.

According to another aspect, a system for determining a measurement of anxiety in a vehicle that includes a memory storing instructions when executed by a processor cause the processor to receive sensor data from a plurality of sensors disposed within a plurality of areas of the vehicle. The instructions also cause the processor to process the sensor data into metrics associated with a type of measurement. Processing of the sensor data is completed by a neural network. The instructions additionally cause the processor to analyze the processed metrics and determining an anxiety level associated with an occupant of the vehicle. The instructions further cause the processor to train the neural network based on the anxiety level and at least one driving event that is correlated with the anxiety level.

According to still another aspect, a non-transitory computer readable storage medium storing instructions that when executed by a computer, which includes a processor perform a method that includes receiving sensor data from a plurality of sensors disposed within a plurality of areas of a vehicle. The method also includes processing the sensor data into metrics associated with a type of measurement. Processing of the sensor data is completed by a neural network. The method additionally includes analyzing the processed metrics and determining an anxiety level associated with an occupant of the vehicle. The method further includes training the neural network based on the anxiety level and at least one driving event that is correlated with the anxiety level.

BRIEF DESCRIPTION OF THE DRAWINGS

The novel features believed to be characteristic of the disclosure are set forth in the appended claims. In the descriptions that follow, like parts are marked throughout the specification and drawings with the same numerals, respectively. The drawing figures are not necessarily drawn to scale and certain figures can be shown in exaggerated or generalized form in the interest of clarity and conciseness. The disclosure itself, however, as well as a preferred mode of use, further objects and advances thereof, will be best understood by reference to the following detailed description of illustrative embodiments when read in conjunction with the accompanying drawings, wherein:

DETAILED DESCRIPTION

Figure 1:
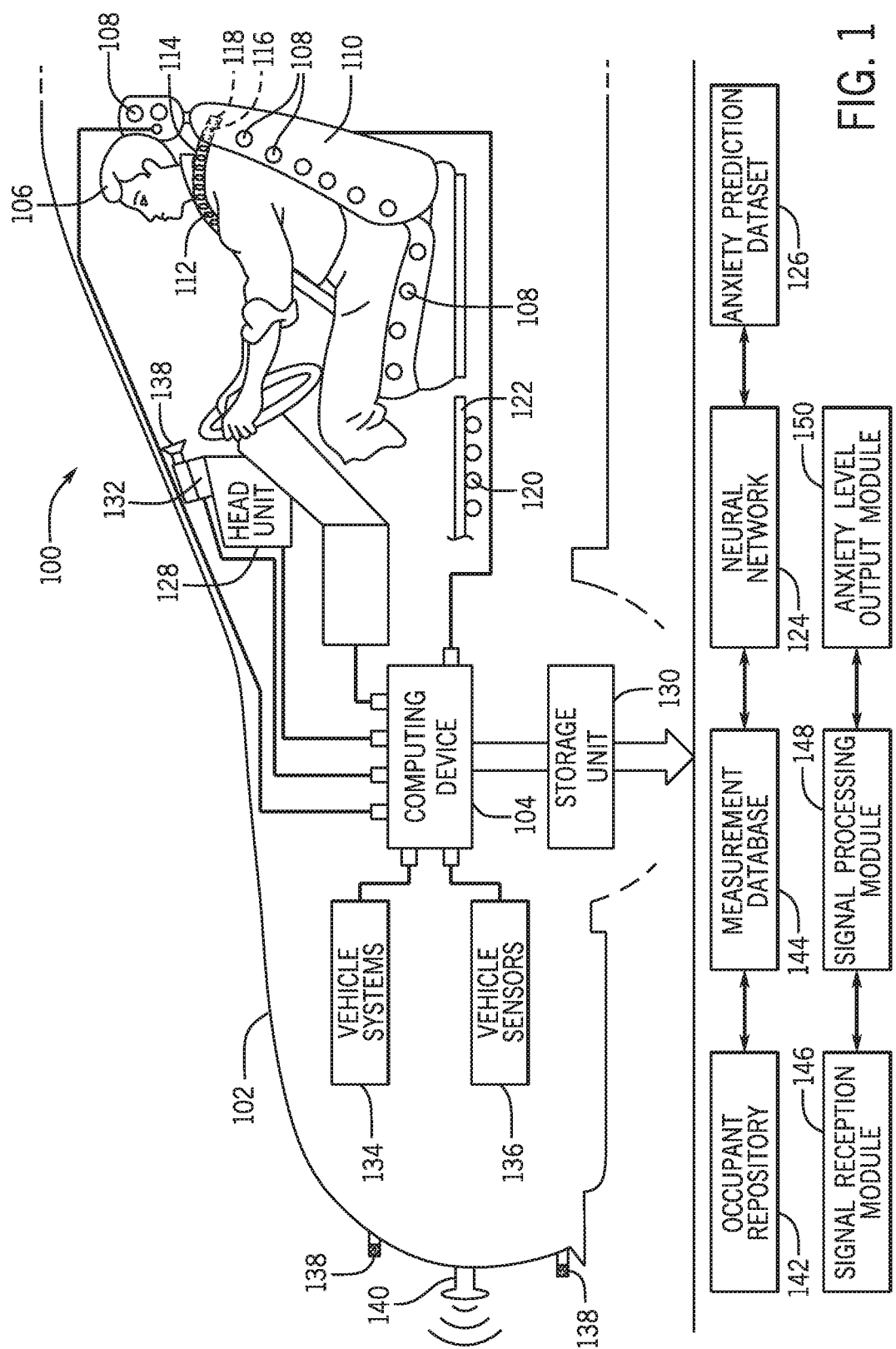
FIG. 1 is a system for implementing systems and methods for completing a measurement of anxiety accordingly to an exemplary embodiment.

The following includes definitions of selected terms employed herein. The definitions include various examples and/or forms of components that fall within the scope of a term and that can be used for implementation. The examples are not intended to be limiting.

A "bus", as used herein, refers to an interconnected architecture that is operably connected to other computer components inside a computer or between computers. The bus can transfer data between the computer components. The bus can be a memory bus, a memory controller, a peripheral bus, an external bus, a crossbar switch, and/or a local bus, among others. The bus can also be a vehicle bus that interconnects components inside a vehicle using protocols such as Media Oriented Systems Transport (MOST), Controller Area network (CAN), Local Interconnect Network (LIN), among others.

"Computer communication", as used herein, refers to a communication between two or more computing devices (e.g., computer, personal digital assistant, cellular telephone, network device) and can be, for example, a network transfer, a file transfer, an applet transfer, an email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, among others.

A "disk", as used herein can be, for example, a magnetic disk drive, a solid state disk drive, a floppy disk drive, a tape drive, a Zip drive, a flash memory card, and/or a memory stick. Furthermore, the disk can be a CD-ROM (compact disk ROM), a CD recordable drive (CD-R drive), a CD rewritable drive (CD-RW drive), and/or a digital video ROM drive (DVD ROM). The disk can store an operating system that controls or allocates resources of a computing device.

A "database", as used herein can refer to table, a set of tables, a set of data stores and/or methods for accessing and/or manipulating those data stores. Some databases can be incorporated with a disk as defined above.

A "memory", as used herein can include volatile memory and/or non-volatile memory. Non-volatile memory can include, for example, ROM (read only memory), PROM (programmable read only memory), EPROM (erasable PROM), and EEPROM (electrically erasable PROM). Volatile memory can include, for example, RAM (random access memory), synchronous RAM (SRAM), dynamic RAM (DRAM), synchronous DRAM (SDRAM), double data rate SDRAM (DDR SDRAM), and direct RAM bus RAM (DR-RAM). The memory can store an operating system that controls or allocates resources of a computing device.

A "module", as used herein, includes, but is not limited to, non-transitory computer readable medium that stores instructions, instructions in execution on a machine, hardware, firmware, software in execution on a machine, and/or combinations of each to perform a function(s) or an action(s), and/or to cause a function or action from another module, method, and/or system. A module may also include logic, a software controlled microprocessor, a discrete logic circuit, an analog circuit, a digital circuit, a programmed logic device, a memory device containing executing instructions, logic gates, a combination of gates, and/or other circuit components. Multiple modules may be combined into one module and single modules may be distributed among multiple modules.

An "operable connection", or a connection by which entities are "operably connected", is one in which signals, physical communications, and/or logical communications can be sent and/or received. An operable connection can include a wireless interface, a physical interface, a data interface and/or an electrical interface.

A "processor", as used herein, processes signals and performs general computing and arithmetic functions. Signals processed by the processor can include digital signals, data signals, computer instructions, processor instructions, messages, a bit, a bit stream, or other means that can be received, transmitted and/or detected. Generally, the processor can be a variety of various processors including multiple single and multicore processors and co-processors and other multiple single and multicore processor and co-processor architectures. The processor can include various modules to execute various functions.

A "portable device", as used herein, is a computing device typically having a display screen with user input (e.g., touch, keyboard) and a processor for computing. Portable devices include, but are not limited to, handheld devices, mobile devices, smart phones, laptops, tablets and e-readers. In some embodiments, a "portable device" could refer to a remote device that includes a processor for computing and/or a communication interface for receiving and transmitting data remotely.

A "vehicle", as used herein, refers to any moving vehicle that is capable of carrying one or more human occupants and is powered by any form of energy. The term "vehicle" includes, but is not limited to: cars, trucks, vans, minivans, SUVs, motorcycles, scooters, boats, go-karts, amusement ride cars, rail transport, personal watercraft, and aircraft. In some cases, a motor vehicle includes one or more engines. Further, the term "vehicle" can refer to an electric vehicle (EV) that is capable of carrying one or more human occupants and is powered entirely or partially by one or more electric motors powered by an electric battery. The EV can include battery electric vehicles (BEV) and plug-in hybrid electric vehicles (PHEV). The term "vehicle" can also refer to an autonomous vehicle and/or self-driving vehicle powered by any form of energy. The autonomous vehicle may or may not carry one or more human occupants. Further, the term "vehicle" can include vehicles that are automated or non-automated with pre-determined paths or free-moving vehicles.

A "vehicle system", as used herein can include, but is not limited to, any automatic or manual systems that can be used to enhance the vehicle, driving and/or safety. A "vehicle system", as used herein can include, but is not limited to, any automatic or manual systems that can be used to enhance the vehicle, driving and/or safety. Exemplary vehicle systems include, but are not limited to: an electronic stability control system, an anti-lock brake system, a brake assist system, an automatic brake prefill system, a low speed follow system, a cruise control system, a collision warning system, a collision mitigation braking system, an auto cruise control system, a lane departure warning system, a blind spot indicator system, a lane keep assist system, a navigation system, a transmission system, brake pedal systems, an electronic power steering system, visual devices (e.g., camera systems, proximity sensor systems), a climate control system, an electronic pretensioning system, a monitoring system, a passenger detection system, a vehicle suspension system, a vehicle seat configuration system, a vehicle cabin lighting system, an audio system, a sensory system, among others.

A "wearable computing device", as used herein can include, but is not limited to, a computing device component (e.g., a processor) with circuitry that can be worn by and/or in possession of a user. In other words, a wearable computing device is a computer that is subsumed into the personal space of a user. Wearable computing devices can include a display and can include various sensors for sensing and determining various parameters associated with a user. For example, location, motion, and biosignal (physiological) parameters, among others. Some wearable computing devices have user input and output functionality. Exemplary wearable computing devices can include, but are not limited to, watches, glasses, clothing, gloves, hats, shirts, jewelry, rings, earrings necklaces, armbands, shoes, earbuds, headphones and personal wellness devices.

I. System Overview

Referring now to the drawings, wherein the showings are for purposes of illustrating one or more embodiments and not for purposes of limiting the same, FIG. 1 illustrates a system 100 for implementing systems and methods for completing a measurement of anxiety according to an exemplary embodiment. The system 100 illustrated in FIG. 1 may be implemented within a vehicle 102. However, it is to be appreciated that the components of the system 100, as well as the components of other systems and architectures discussed herein, may be combined, omitted or organized into different architectures for various embodiments. It is also to be appreciated, that other components not shown in FIG. 1, (e.g., communication units/gateways, communication networks, and buses) or several instances of the components shown in FIG. 1 can also be included.

In an exemplary embodiment, the system 100 may include a computing device 104 that may include a plurality of processing modules (discussed below) that may be utilized with additional components of the vehicle 102 to determine an anxiety level associated with a particular individual. As discussed in more detail below, the computing device 104 may be configured to communicate with various sensors disposed within a plurality of areas of the vehicle 102 to sense various readings that may be analyzed to determine the anxiety level of the particular individual, which may include, but may not be limited to an occupant 106 (e.g., driver, non-driving passenger) within the vehicle 102. For purposes of simplicity, this disclosure will discuss the applicability of components and processes with respect to the occupant 106 of the vehicle 102. However, it is appreciated that the components and processes discussed herein may apply to individuals outside of a vehicular environment.

The computing device 104 may be configured to communicate with a plurality of seat sensors 108 disposed within a seat back, an arm rest, a seat cushion, a head rest, and the like of a seat 110 of the vehicle 102 on which the occupant 106 is seated. Additionally, the computing device 104 may be configured to communicate with a plurality of seat belt sensors 112 disposed within a seat belt 114 and plurality of encoder sensors 116 that may be configured within an encoder 118. The encoder 118 may be included as part of a seat belt retractor or seat belt winding mechanism (not shown). The computing device 104 may additionally be configured to communicate with a plurality of floor sensors 120 that are disposed within a floor board 122 (e.g., foot well) of the vehicle 102 that may be located adjacent to the seat 110 in which the occupant 106 is seated.

As discussed below, the plurality of seat sensors 108 and the plurality of seat belt sensors 112 may output sensor data pertaining to pressure sensor readings from pressure sensors and biometric sensor readings from flex sensors that may be received by the computing device 104 to be further processed. The plurality of floor sensors 120 may output sensor data pertaining to pressure sensor readings from pressure sensors that pertain to levels of pressure (force) that are applied to the floor board 122 that may be received by the computing device 104 to be processed. Additionally, the plurality of encoder sensors 116 may be configured as flex sensors that may sense levels of stress placed upon the seat belt 114 that may be received by the computing device 104 to be processed.

As discussed in more detail below, the computing device 104 may be configured to store the sensor data for one or more predetermined periods of time. Additionally, the computing device 104 may be configured to filter the sensor data to remove noise associated with the movement of the vehicle 102. The computing device 104 may also be configured to utilize a neural network 124 to process the sensor data into metrics that may pertain to a state of anxiousness exhibited by the occupant 106 during the course of travel (e.g., driving, seated as a non-driving passenger) within the vehicle 102.

In one embodiment, the metrics processed by the neural network 124 may include, but may not be limited to, one or more metrics corresponding to a body position (e.g., body language that may pertain to anxiety) of the occupant 106, one or more metrics corresponding to a level of fidgeting (e.g., small movements that may indicate anxiety) exhibited by the occupant 106, and one or more metrics corresponding to a ventilation rate (e.g., breathing rate that may pertain to anxiety) exhibited by the occupant 106. It is contemplated that the computing device 104 and/or the neural network 124 may be configured to output additional metrics that may pertain to a state of anxiousness and/or additional biometric/emotional states that may be exhibited by an individual such as the occupant 106 (e.g., alertness, heart rate, head movement rate).

In one or more embodiments, the computing device 104 may additionally utilize the neural network 124 to execute machine learning/deep learning to provide artificial intelligence capabilities that may be utilized to analyze the metrics and determine an anxiety level associated with the occupant 106 of the vehicle 102 that is output to the computing device 104. In one embodiment, the computing device 104 may be configured to train the neural network 124 based on the anxiety level outputted by the neural network 124 to add data to an anxiety prediction dataset 126 of the neural network 124.

The anxiety prediction dataset 126 may be included as an electronic data model that correlates one or more driving events that simultaneously take place when sensor readings are captured and processed into to one or more of the metrics that are further analyzed to determine the anxiety level. The one or more driving events may include one or more driving conditions that may occur within a surrounding environment of the vehicle 102 (e.g., a predetermined vicinity of the vehicle 102).

Such conditions may include, but may not be limited to, a position, location, and direction of one or more additional traffic participants (e.g., other vehicles and pedestrians) within the surrounding environment of the vehicle 102 that may affect how the vehicle 102 is driven/operated (e.g., speed, braking, turning, etc.). Additionally, the one or more driving events may include the location of one or more objects (e.g., construction cones, trees, light posts, etc.) that may be located within the surrounding environment of the vehicle 102 that may affect how the vehicle 102 is driven/operated.

The one or more driving events may also include the characteristics of one or more roadways including the roadway on which the vehicle 102 is traveling, one or more traffic signals, and one or more traffic signs that may also affect how the vehicle 102 is driven/operated. The one or more driving events may additionally include one or more vehicle dynamics associated with how the vehicle 102 is operated based on the characteristics of one or more roadways including the roadway on which the vehicle 102 is traveling, one or more traffic signals, and one or more traffic signs that may also affect how the vehicle 102 is driven/operated. For example, the one or more driving events may also include data pertaining to vehicle dynamics including, but not limited to the speed, brake pressure, steering angle, acceleration, turn signal usage, etc. of the vehicle 102 based on the characteristics of one or more roadways including the roadway on which the vehicle 102 is traveling, one or more traffic signals, and one or more traffic signs that may also affect how the vehicle 102 is driven/operated.

In an exemplary embodiment, the computing device 104 may be configured to correlate (e.g., electronically pair, link) one or more anxiety levels with one or more particular driving events and add the correlated data within the anxiety prediction dataset 126 to thereby train the neural network 124 to predict when the occupant 106 may experience a particular level of anxiety based on the occurrence of one or more similar driving events (that may be occurring in real-time) based on analysis of the dataset 126. In additional embodiments, the computing device 104 may be configured to present one or more interfaces and/or provide one or more vehicle system controls to provide feedback and/or autonomous or semi-autonomous control of the vehicle 102 based on one or more driving events, determined real-time levels of anxiety associated with the occupant 106, and/or predicted levels of anxiety associated with the occupant 106.

With particular reference to the vehicle 102 of FIG. 1, the computing device 104 may be configured to operably control one or more components of the vehicle 102. In one embodiment, the computing device 104 may include a microprocessor, one or more application-specific integrated circuit(s) (ASIC), or other similar devices. The computing device 104 may also include internal processing memory, an interface circuit, and bus lines for transferring data, sending commands, and communicating with the plurality of components of the vehicle 102.

The computing device 104 may also include a communication device (not shown) for sending data internally in the vehicle 102 and communicating with externally hosted computing systems (e.g., external to the vehicle 102). Generally, the computing device 104 communicates with a head unit 128 and a storage unit 130 of the vehicle 102 to execute one or more applications, operating systems, vehicle system and subsystem user interfaces, and the like that may be stored on the storage unit 130.

In one or more embodiments, the computing device 104 may include a computation stack (not shown) that may be utilized to pool and aggregate sensor data received from the plurality of sensors 108, 112, 116, 120 to thereby be aggregated and populated within a measurement database 144 of the neural network 124. In one exemplary embodiment, the computation stack of the computing device 104 may be configured as a series of single-board computers that may be configured to process and pool various types of sensor data received from the plurality of sensors 108, 112, 116, 120.

In an exemplary embodiment, the computing device 104 may be operably connected to the head unit 128 of the vehicle 102. The head unit 128 may be operably connected to the display unit 132 and/or one or more additional display units (not shown) (e.g., display screens), audio devices (not shown), and haptic devices (not shown) (e.g., haptic steering wheel) that are utilized to provide a human machine interface (not shown). The display unit 132 may be operated to display one or more user interfaces that may present one or more graphical interface objects pertaining to alerts, vehicle system information, and/or additional operational data.

In an exemplary embodiment, the vehicle systems 134 of the vehicle 102 may include one or more systems that may be utilized to autonomously control the vehicle 102 and/or one or more functions of the vehicle 102. The vehicle systems 134 may include, but are not limited to, any automatic or manual systems that may be used to enhance vehicle driving. For example, the vehicle systems 134 may include Advanced Driver Assistance Systems (ADAS), for example, an adaptive cruise control system, a blind spot monitoring system, a collision mitigation system, a lane departure warning system, among others that may be utilized to provide warnings/alerts to the occupant 106 (and/or additional occupants of the vehicle 102) that may be based on the outputted occupant anxiety level and/or one or more driving events.

As discussed, one or more driving events that simultaneously take place when sensor readings are captured and are processed into to one or more of the metrics may be correlated with the determined anxiety level of the occupant 106. In one or more embodiments, the one or more driving events may be determined by the computing device 104 based on the utilization of vehicle environmental and vehicle sensors 136 of the vehicle 102.

The vehicle sensors 136 may include visual sensors in the form of cameras 138 that may be mounted on one or more external portions of the vehicle 102 including, but not limited to different portions of the vehicle dashboard, vehicle bumper, vehicle front lighting units, vehicle fenders, and the windshield (portions of the vehicle 102 not shown). The cameras 138 may also be mounted on one or more internal portions of the vehicle 102 to capture images of the occupant 106 including, but not limited to, above the head unit 128 and/or display unit 132. For example, one or more of the cameras 138 may be positioned to face the occupant 106 to capture images of the occupant 106 seated within the seat 110. One or more of the cameras 138 may also be positioned at one or more areas of the surrounding environment of the vehicle 102 and may be configured to capture images/video around (front/sides/behind) the vehicle 102 (e.g., road environment in front, sides, and/or behind of the vehicle 102) that may be included within the vehicle's travel path.

In one embodiment, the computing device 104 may utilize the display unit 132 to present an occupant setup user interface (not shown). In one configuration, the occupant setup user interface may be configured to be presented based on the detection (e.g., identification) of the occupant 106 by one or more of the cameras 138. For example, as shown in FIG. 1, one or more cameras 138 disposed near the display unit 132 within the vehicle 102 may be positioned to capture images of the occupant 106 to detect (e.g., identify) a particular occupant 106. In one configuration, the detection of the particular occupant 106 may be completed based on the execution of machine vision (e.g., utilizing image logic, face recognition logic) to identify the particular occupant 106 that is seated within the seat 110.

Upon detection of the particular occupant 106, the occupant setup user interface may allow the particular occupant 106 to setup an occupant profile (not shown) that is associated with the particular occupant 106. In particular, the occupant profile that is associated with the occupant 106 may be used to further identify the occupant 106 and associate the processed metrics and the determined anxiety level to the particular occupant 106. This functionality may ensure that the neural network 124 is subjectively trained to determine and predict anxiety level(s) that are specifically associated with the particular occupant 106 based on metrics that are subjectively analyzed for the particular occupant 106. In some configurations, if the particular occupant 106 or a previously detected occupant is not detected based on the execution of machine vision by one or more cameras 138, the computing device 104 may utilize the occupant setup user interface to setup an occupant profile to provide user identification information that may be utilized to subjectively associate one or more determined anxiety levels to a (new) occupant 106.

With continued reference to the vehicle sensors 136, in additional embodiments, the vehicle sensors 136 may additionally include LiDAR transceivers 140 that may be disposed at the aforementioned external front and/or side portions of the vehicle 102. In one configuration, one or more of the LiDAR transceivers 140 may include one or more planar sweep lasers that include respective three-dimensional LiDAR sensors that may be configured to oscillate and emit one or more laser beams of ultraviolet, visible, or near infrared light toward the surrounding environment of the vehicle 102. The LiDAR transceivers 140 may be configured to receive one or more reflected laser waves (e.g., signals) that are reflected off one or more objects included within the surrounding environment of the vehicle 102.

In one or more embodiments, the vehicle sensors 136 may also be configured as specific types of sensors that provide vehicle operation related information that may include, but may not be limited to, vehicle mileage sensors, vehicle speed sensors, vehicle acceleration sensors, vehicle angular velocity sensors, accelerator pedal sensors, brake sensors, steering wheel angle sensors, vehicle directional sensors (e.g., vehicle compass), throttle position sensors, respective wheel sensors, anti-lock brake sensors, camshaft sensors, among other sensors.

Additionally, the vehicle sensors 136 may be configured as specific types of sensors that provide data pertaining to road conditions and the surrounding environment of the vehicle 102, such as, but not limited to, antilock brake sensors, daylight sensors, temperature sensors, wheel slip sensors, traction control sensors, etc. It is understood that the vehicle sensors 136 may be any type of sensor, for example, acoustic, electric, environmental, optical, imaging, light, pressure, force, thermal, temperature, proximity, among others. As discussed below, the computing device 104 may be configured to execute computer logic (e.g., software image and LiDAR data evaluation logic) to aggregate sensor data from the vehicle sensors 136 and determine one or more driving events that occur at particular points in time (associated with particular time stamps) as the vehicle 102 is being operated.

Figure 2:
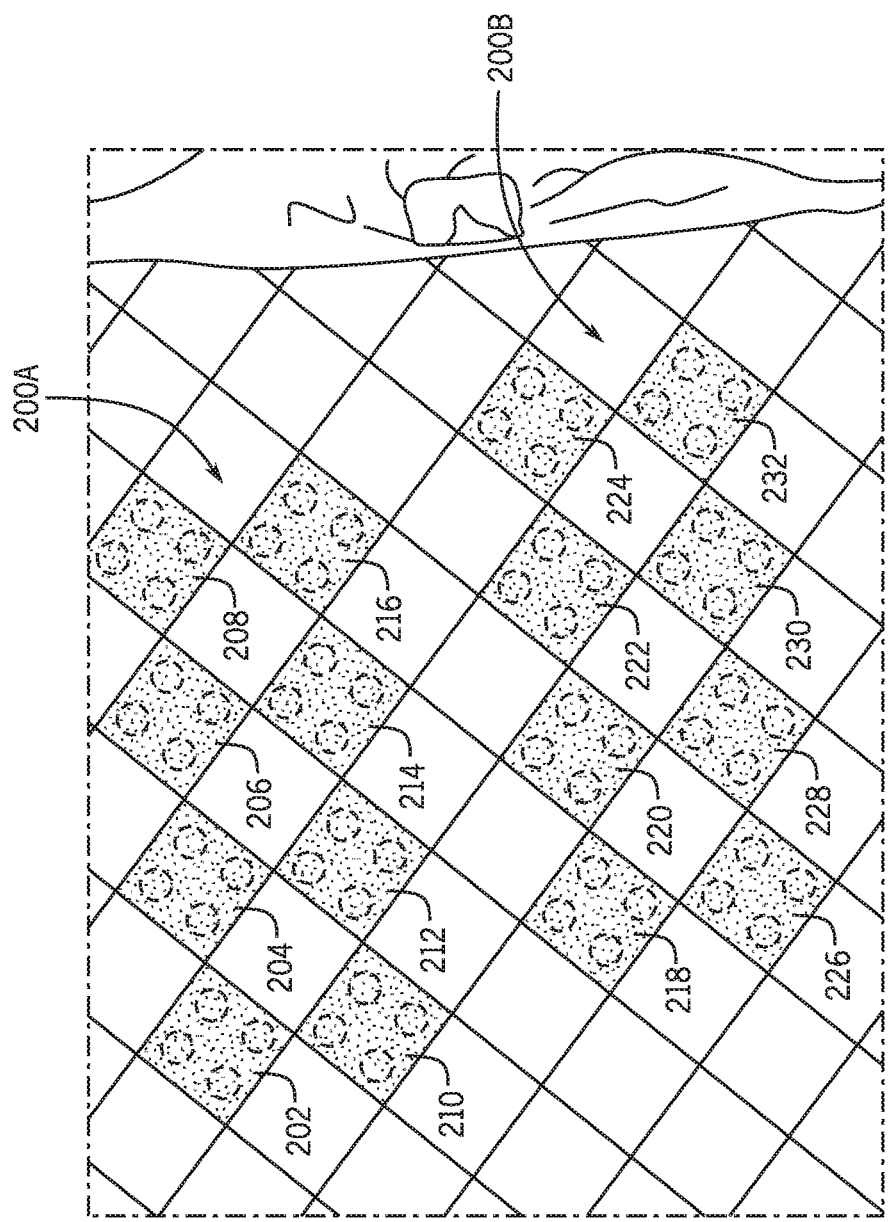
FIG. 2 is an illustrative example of the plurality of seat sensors according to an exemplary embodiment.

With particular reference to the plurality of sensors 108, 112, 116, 120, as discussed above, the seat 110 of the vehicle 102 may include the plurality of seat sensors 108. FIG. 2 is an illustrative example of the plurality of seat sensors 108 according to an exemplary embodiment. As represented in FIG. 2, the plurality of sensors 108 may be configured in one or more N×N matrices 200A, 200B of pressure sensors (not specifically shown) and flex sensors (not specifically shown). In particular, the pressure sensors may be disposed in one or more matrices 200A, 200B to provide a pressure sensing map that may be utilized to sense the body position and movements of the occupant 106 based on a change of pressure/pressure distribution over time upon one or more portions of the seat 110.

As an illustrative example, the pressure sensing map may be based on pressure sensors that may be located at each of the zones 202-216 of the matrix 200A and each of the pressure sensors that may be located at each of the zones 218-232 of the matrix 200B (and additional pressures sensors or additional zones, not shown). The pressure sensing map may be utilized to determine readings of pressure distribution of the occupant 106 within the seat 110 as sensed by one or more pressure sensors of the plurality of seat sensors 108 at one or more zones 202-232 of the matrices 200A, 200B for one or more predetermined periods of time.

Stated differently, the pressure distribution may be determined based on sensor data that includes a measurement of an amount of force applied (e.g., in psi) as sensed by pressure sensor readings in each of the respective zones 202-232 of the matrices 200A, 200B to output readings of pressure distribution associated with the occupant 106 within the seat 110. Such readings of pressure distribution may be output by one or more pressure sensors as sensor data that may be analyzed by the neural network 124 during processing to determine changes in a body position of the occupant 106, a level of fidgeting exhibited by the occupant 106, and/or a ventilation rate exhibited by the occupant 106 for the predetermined period(s) of time.

In one embodiment, the flex sensors may specifically include, but may not be limited to electromyograms and/or electrocardiograms, moisture sensors, thermistors, and the like that may detect various biometric sensing readings that may be provided in the form of one or more sensor signals. Accordingly, the flex sensors may be arranged in the matrices 200A, 200B to be utilized to detect a body position of the occupant 106, a ventilation (e.g., breathing) rate exhibited by the occupant 106, and/or fidgeting that may be exhibited by the occupant 106. In one configuration, the flex sensors may also be disposed within the matrices 200A, 200B at areas that may be located near areas of the occupant's body that have thinner layers of skin (e.g., ear lobes, finger tips) and/or expected thin areas of clothing of the occupant 106 to capture biometric readings associated with the occupant 106. It is to be appreciated that the flex sensors may be configured to sense various additional contemplated biometric parameters associated with the occupant 106.

In one embodiment, the plurality of seat sensors 108 may be disposed within one or more types of materials/fabrics that may be included as a top, outer, or inner layer of material of the seat 110 the vehicle 102. In some configurations, the plurality of seat sensors 108 may be disposed on an underside of an outermost material/fabric layer of the seat 110, such that the plurality of seat sensors 108 are not disposed on an exterior surface of the seat 110 and are not visible to the occupant 106. In additional embodiments, the matrices 200A, 200B of pressure sensors and flex sensors may be included as a network of sensors that may be disposed within sensing materials/fabrics of the seat 110. For example, the pressure sensors and flex sensors may be disposed as part of piezoresistive and/or capacitive fabrics interwoven with one another and into the seat 110 with conductive thread. The cross-stitching of the thread may elucidate an array of variable impendences/capacitances that may be utilized to determine pressure sensing values and/or additional biometric measuring values that may be evaluated during processing of the metrics by the neural network 124, as discussed below.

One or more of the plurality of seat belt sensors 112 may be similarly configured with pressure sensors and flex sensors that may be disposed within one or more matrices (not shown) upon the seat belt 114. With respect to the pressure sensors and flex sensors disposed upon the seat belt 114 itself, the pressure sensors and flex sensors may include similar functionality and circuitry to the pressure sensors and flex sensors of the plurality of seat sensors 108 and the plurality of seat belt sensors 112.

The pressure sensors and the flex sensors may be disposed within one or more types of materials/fabrics that may be included as a top or inner layer of material of the seat belt 114. In some configurations, the plurality of seat belt sensors 112 may be disposed on an underside of an outermost material/fabric layer of the seat belt 114 (e.g., facing the body of the occupant 106), such that the plurality of seat belt sensors 112 are not disposed on an exterior surface of the seat belt 114 and are not visible to the occupant 106. In additional embodiments, one or more matrices of pressure sensors and flex sensors may be included as a network of sensors that may be disposed within sensing materials/ fabrics of the seat belt 114. For example, the pressure sensors and flex sensors may be disposed as part of piezoresistive and/or capacitive fabrics interwoven with one another and into the seat belt 114 with conductive thread.

In one or more embodiments, as discussed below, biometric information captured by the flex sensors of the plurality of seat sensors 108 and the plurality of seat belt sensors 112 may be utilized in collaboration to sense biometric parameters associated with the occupant 106. For example, flex sensors included as part of the plurality of seat sensors 108 and the plurality of seat belt sensors 112 may be utilized in conjunction to detect a level of sweat of the occupant 106, body heat of the occupant 106, and/or a heart rate of the occupant 106. These measurements and measurements pertaining to the change in a body position, the level of fidgeting, and/or the ventilation rate exhibited by the occupant 106 for the predetermined period(s) of time may also be provided as sensor data that may be processed into metrics by the neural network 124.

In an exemplary embodiment, the plurality of encoder sensors 116 of the encoder 118 may be configured as flex sensors that may sense levels of stress placed upon the seat belt 114 to thereby detect a body language exhibited by the occupant 106, a ventilation rate exhibited by the occupant 106 and/or fidgeting that may be exhibited by the occupant 106. In one configuration, the seat belt 114 may be positioned between the encoder 118 and one or more rollers and/or retractors (not shown) which allow the seat belt 114 to roll outwards and/or retract inwards from a housing that may be disposed behind vehicle paneling (not shown) or may be encased and attached to the seat 110.

In one configuration, the plurality of encoder sensors 116 may output signals that include a binary code which may correspond to a number of rotations of a pin that is attached to the roller to rotate the seat belt 114. The signals may include a number of forward rotations and/or backward rotations of the pin to thereby capture a frequency and amount of outward rolling or retraction of the seat belt 114 caused by the occupant 106 seated within the seat 110. Accordingly, the sensors of the encoder 118 may be configured to sense a level of stress (e.g., pull) placed on the seat belt 114 and may output respective measurements as sensor data.

As discussed below, the computing device 104 may collect sensor data pertaining to the sensor measurements for a predetermined period(s) of time from the plurality of encoder sensors 116 and may thereby determine a change in levels of stress and pull on the seat belt 114 in order for the neural network 124 to analyze how much and how rapidly the stress on the seat belt 114 changes during the predetermined period(s) of time to thereby process one or more metrics. For example, if the plurality of encoder sensors 116 provide sensor data that indicate that the occupant 106 has greatly extended the seat belt 114 based on a large value associated with an outward rolling of the seat belt 114 over the predetermined period(s) of time, metrics may indicate that a body position of the occupant 106 is tense.

With particular reference to the plurality of floor sensors 120, the plurality of floor sensors 120 may include pressure sensors that may be configured in one or more arrays that may be configured to sense an amount of force that the occupant's feet are applying to one or more portions of the floor board 122. In particular, the one or more arrays of pressure sensors may be configured to sense the force of the occupant's feet at one or more portions of the floor board 122 to determine rapid tapping of the occupant's feet (that may indicate anxiousness based on greater likelihood of tension exhibited by the occupant 106).

In one configuration, the plurality of floor sensors 120 may be disposed on an underside of an outermost layer of the floor board 122, such that the plurality of floor sensors 120 are not disposed on an exterior surface of the floor board 122 and are not visible to the occupant 106. In some embodiments, the plurality of floor sensors 120 may be arranged in a matrix pattern (similar to the matrix 200A) that may include one or more matrices beneath/attached to the floor board 122 of the vehicle 102. The matrix pattern may thereby be utilized as a floor pressuring sensing map that may sense a level of pressure and force that may be applied to one or more zones (not shown) of one or more matrices to measure foot tapping associated with the occupant 106. As discussed below, the computing device 104 may collect data for a predetermined period(s) of time from the plurality of floor sensors 120 and may input filtered sensor data to the neural network 124 to process and determine a pressure distribution upon the floor board 122 based on a change in foot placement of the occupant 106 in order for the neural network 124 to analyze how rapidly the occupant 106 taps their foot/feet.

As discussed in more detail below, one or more sensor signals may be output by the plurality of seat sensors 108, the plurality of seat belt sensors 112, the plurality of encoder sensors 116, and the plurality of floor sensors 120 along with time stamps (e.g., data files) that indicate times at which data is sensed and is communicated to the computing device 104. Such data may be communicated in one or more signals that include sensor data packets that may be received to be filtered to remove noise artifacts and further be inputted to the neural network 124 to be processed into metrics. As discussed in more detail, the neural network 124 may complete processing of the sensor data to determine one or more metrics that may be further analyzed to determine and output the anxiety level of the occupant 106.

With particular reference to the storage unit 130, in one or more embodiments, the computing device 104 may be operably connected to the storage unit 130 as an independent component of the vehicle 102. In an alternate embodiment, the storage unit 130 may be included as a component of the head unit 128. The storage unit 130 may store one or more operating systems, associated operating system data, applications, associated application data, vehicle system and subsystem user interface/application data, and the like that are executed by the computing device 104 and/or the head unit 128 of the vehicle 102. In one configuration, the storage unit 130 may store an occupant repository 142 that may be configured as a data storage repository that is configured to store data. In one embodiment, if the occupant 106 utilizes the occupant setup user interface (discussed above) to create an associated occupant profile, the computing device 104 may access the storage unit 130 and may populate the occupant repository 142 with the associated occupant profile.

In one embodiment, the occupant profile may be populated with various user identification information based on inputs provided by the occupant 106 through the occupant setup user interface. Such information may include, but may not be limited to, the occupant's name, user ID (e.g., selected user identification, credentials such as user name/password), the occupant's age, gender, height, weight, and/or additional biometric identifying information that may be populated through communication with one or more external devices (e.g., wearable devices that provide identifying and/or biometric information).

In addition to the occupant repository 142, the storage unit 130 may be configured to store the measurement database 144, the neural network 124, and the anxiety prediction dataset 126. With particular reference to the measurement database 144, the database 144 may be configured as a relational database that may include a plurality of records and fields that are structured to recognize relations among various user identification information based on inputs provided by the occupant 106 through the occupant setup user interface and stored within the occupant profile.

In particular, one or more records and associated (e.g., underlying) fields may be populated by the computing device 104 with occupant identification information, sensor data, and timestamp data based on a timestamp associated with sensor readings that may be captured by the plurality of sensors 108, 112, 116, 120. The measurement database 144 may be utilized to store the sensor data and associated time stamp data as further sensor data is received for a predetermined period(s) of time from the plurality of sensors 108, 112, 116, 120.

The measurement database 144 may be further queried by the computing device 104 to retrieve the signal data received for the predetermined period(s) of time to be filtered and further processed into metrics. In one embodiment, upon the processing of metrics by the neural network 124, the computing device 104 may access the measurement database 144 and may create one or more records with metrics data captured for the predetermined period(s) of time and associated timestamp data associated to the sensor data pertaining to the metrics.

As discussed above, the anxiety prediction dataset 126 may be included as an independent data model that correlates one or more driving events that simultaneously take place when sensor readings are captured that are processed into one or more of the metrics. In an alternate embodiment, the anxiety prediction dataset 126 may be included as a subset or sub-component of the measurement database 144. In one configuration, the anxiety prediction dataset 126 may be configured as an electronic collection of related sets of information that is composed of separate elements but can be manipulated as a unit by the computing device 104 and/or the neural network 124.

In an exemplary embodiment, the computing device 104 may be configured to correlate (e.g., electronically pair, link) one or more anxiety levels outputted by the neural network 124 to one or more particular driving events within the anxiety prediction dataset 126 to thereby train the neural network 124 to predict when the occupant 106 may experience a particular level of anxiety that may be based on one or more driving events (that may be occurring in real-time) based on analysis of the dataset 126.

II. Overview of the Structure and Functionality of the Neural Network

With particular reference to the structure of the neural network 124, as discussed, the neural network 124 and/or one or more layers of the neural network 124 may be stored on the storage unit 130. In additional embodiments, one or more layers of the neural network 124 may be stored on an externally hosted computing infrastructure (not shown) external to the vehicle 102 and may be accessed by the communication device of the computing device 104.

Figure 3:
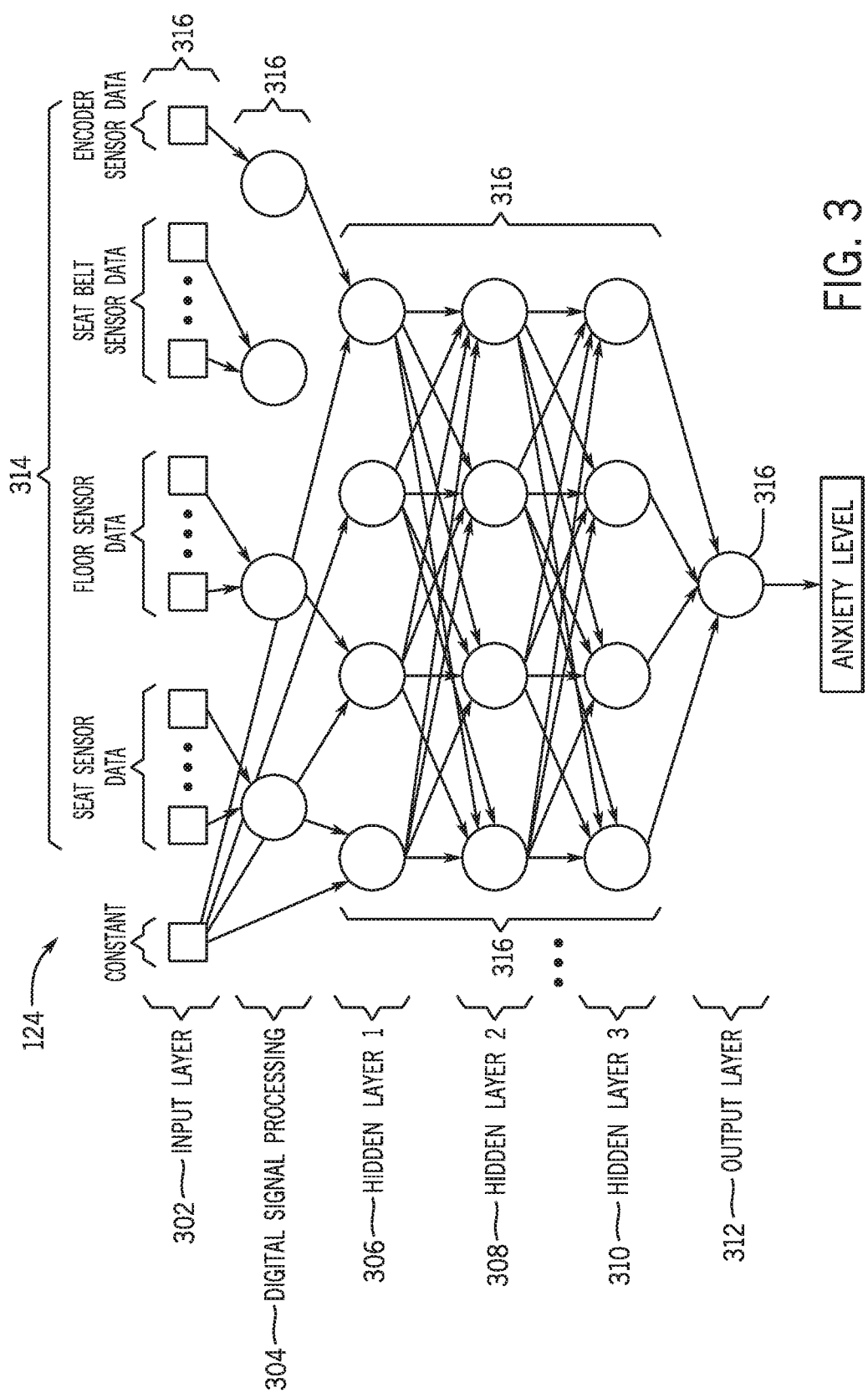
FIG. 3 is a software schematic of a neural network configured as a shallow neural network according to an exemplary embodiment.

FIG. 3 includes a software schematic of the neural network 124 configured as a shallow neural network according to an exemplary embodiment. In one embodiment, the neural network 124 may include a plurality of fully connected layers (plurality of layers) 302-312. In an alternate embodiment, the neural network 124 may be configured as a multi-stream Recurrent Neural Network (RNN) and may include an encoder-decoder structure that includes the plurality of fully connected layers 302-312. In yet an additional alternate embodiment, the neural network 124 may be configured as a convolutional neural network (CNN) that may be configured to receive inputs in a form of sensor data streams and may flatten the data and concatenate the data into processed metrics.

With reference to the exemplary structure of the neural network 124 illustrated in FIG. 3, the neural network 124 may process a programming model which enables computer/machine based/deep learning that may be centered on one or more forms of data that are inputted to the neural network 124. Each of the layers 302-312 of the neural network 124 may include perceptrons 316 which may consist of respective algorithms for supervised learning of binary classifiers. The perceptrons 316 of the layers 302-312 may utilize artificial intelligence processes to analyze, compare, and determine data.

Each of the perceptrons 316 may include a respective weight value (e.g., indicating a vector of real-valued weights) associated with its output. The weight value associated with the output of each perceptron 316 may allow the neural network 124 to process several inputs independently by each perceptron 316 in various forms of sensor data 314 derived from sensor signals provided by the plurality of sensors 108, 112, 116, 120. The processing of the inputs by the perceptrons 316 at one or more layers 302-312 of the neural network 124 may be utilized to determine a single binary or sigmoidal value that pertains to the anxiety level of the occupant 106 that is further output to the computing device 104.

The layers of the neural network 124 may include an input layer 302, a digital signal processing layer 304, two or more hidden layers 306-310, and an output layer 312. Is it to be appreciated that the neural network 124 may include various types of additional layers that are not disclosed herein or included within the schematic embodiment illustrated in FIG. 3. In one configuration, the perceptrons 316 of the input layer 302 of the neural network 124 may be configured to receive inputs of real world data that includes sensor data 314. As discussed in more detail below, the digital signal processing layer 304 may include digital signal processing code (DSP) that may utilize information based on the pre-training of the neural network 124.

More specifically, the neural network 124 may be pre-trained with one or more subsets of data that pertain to one or more stored levels of metrics that may be translated into the DSP and evaluated against processed metrics based on sensor data 314 inputted to the neural network 124. The pre-training of the neural network 124 may be completed by a third-party such as a vehicle manufacturer or third-party organization based on numerous hours of real-world driving scenarios, captured sensor data pertaining to the body position of one or more training subjects, fidgeting exhibited by one or more training subjects, and a ventilation rate exhibited by one or more training subjects when one or more driving events are simultaneously occurring. For example, the pre-training of the neural network 124 may include capturing of sensor data pertaining to a fidgeting level of a training subject for a predetermined period(s) of time that occurs when the vehicle 102 is suddenly stopped at a high braking rate based on another vehicle suddenly stopping in front of the vehicle 102.

The input and output of data by the neural network 124 may begin based on the operation of the computing device 104. In an exemplary embodiment, upon receiving respective sensor data by the plurality of sensors 108, 112, 116, 120 (as discussed in more detail below), the computing device 104 may communicate sensor data to be populated within the measurement database 144 for the predetermined(s) period of time.

In one embodiment, the computing device 104 may access the measurement database 144 to retrieve the sensor data and may utilize one or more noise filtering processes to filter noise from the sensor data inputted from the plurality of sensors 108, 112, 116, 120 (as discussed below). Upon filtering the noise from the sensor data, the computing device 104 may input noise filtered signal data as provided by the plurality of sensors 108, 112, 116, 120 and filtered by the computing device 104 to the neural network 124. Additionally, the computing device 104 may utilize computer logic to determine one or more driving events and may input driving events data 214 that may be inputted in one or more types of data formats (e.g., data values) to the neural network 124.

In an exemplary embodiment, an input layer 302 of the neural network 124 may receive the sensor data 314 to be further processed using the DSP of the digital signal processing layer 304 of the neural network 124. The digital signal processing layer 304 may thereby process the filtered sensor data using the DSP to convert the filtered (raw) sensor data into metrics and associated timestamps that are configured as a usable format for hidden layers 306-310 to thereby compare against parameters of the pre-trained data to determine the anxiety level of the occupant 106. In particular, the DSP may utilize various types of filtered sensor data 314 and may thereby process metrics that may pertain to the body position of the occupant 106, fidgeting exhibited by the occupant 106, and a ventilation rate exhibited by the occupant 106.

In some embodiments, the DSP may process the metrics into data formats that include values and levels. Such values and levels may include, but are not limited to, a numerical or other kind of value or level such as a percentage, a non-numerical value, a discrete state, a discrete value, a continuous value, among others. For example, in some cases, the value or level of X may be provided as a percentage between 0% and 100%. In other cases, the value or level of X may be provided as a value in the range between 1 and 10. In still other cases, the value or level of X may not be a numerical value, but could be associated with a determined state, such as a normal ventilation state or a hyperventilation state.

In one configuration, the output layer 312 of the neural network 124 may include one or more perceptrons 316 that are configured to output an ultimate determination of the anxiety level of the occupant 106 to the computing device 104 based on the electronic analysis of one or more processed metrics. Accordingly, the perceptrons 316 and layers 302-312 of the neural network 124 may enable a composition of artificial intelligence functions by the neural network 124 that act on the input filtered sensor data and output a binary or sigmoidal value (e.g., Boolean value, flat value) based on the pre-trained data (with sample input data and known output data) that indicates the determination of the anxiety level of the occupant 106 that may be output to the computing device 104 to be further correlated with one or more driving events that simultaneously occur.

III. Overview of the Modules of the Computer Device

Referring again to FIG. 1, in one or more embodiments, the computing device 104 may include a plurality of computing processing modules which may be included as electronic circuits that may provide particular computing functions. In one embodiment, the computing device 104 may be configured to include a signal reception module 146, a signal processing module 148, and an anxiety level output module 150. As discussed in more detail below, the signal reception module 146 may be configured to receive sensor data for a predetermined period(s) of time from the plurality of sensors 108, 112, 116, 120. Upon reception of the sensor data, the signal reception module 146 may be configured to pool the sensor data received from the plurality of sensors 108, 112, 116, 120 and associated timestamps corresponding to a time(s) when the sensor data is captured to thereby be aggregated and populated within one or more respective records and associated fields of the measurement database 144.

In one embodiment, the signal processing module 148 may be configured to execute one or more noise filtering processes to filter noise (e.g., noise artifacts) associated with the movement of the vehicle 102 (e.g., causing noise based on roadway bumps, braking, acceleration, etc.) to thereby output filtered sensor data. The signal processing module 148 may additionally be configured to utilize the neural network 124 to process the filtered sensor data into metrics associated with one or more types of measurements such as body position, a level of fidgeting, and ventilation rate.

The signal processing module 148 may also be configured to populate the measurement database 144 with the processed metrics and timestamps associated with the metrics within one or more respective records and associated fields of the measurement database 144. In one or more embodiments, the signal processing module 148 may also be configured to execute computer logic to aggregate sensor data from the vehicle sensors 136 and determine one or more driving events that occur at particular points in time.

In one embodiment, the anxiety level output module 150 of the computing device 104 may be configured to communicate with the neural network 124 to further electronically analyze the processed metrics using machine learning/deep learning to provide artificial intelligence capabilities that may be utilized to determine and output an anxiety level associated with the occupant 106 of the vehicle 102. As discussed below, the anxiety level output module 150 may thereby add data to the anxiety prediction dataset 126 that pertains to the anxiety level of the occupant 106 and one or more driving events that may be correlated to the determined anxiety level to train the neural network 124.

In an exemplary embodiment, the anxiety level output module 150 may be configured to correlate the one or more driving events (determined by the signal processing module 148 based on sensor data output by the vehicle sensors 136) with one or more levels of anxiety output by the neural network 124 to train the neural network 124 by populating data to the anxiety prediction dataset 126. Such data may be utilized by the computing device 104 to present one or more interfaces and/or provide one or more vehicle system controls to provide feedback and/or autonomous or semi-autonomous control of the vehicle 102 based on one or more driving events, determined real-time levels of anxiety associated with the occupant 106, and/or predicted levels of anxiety associated with the occupant 106.

III. Methods Executed by the Computer Device for Completing a Measurement of Anxiety of the Occupant In one embodiment, the computing device 104 may prompt the occupant 106 to identify themselves through the occupant identification user interface presented through the display unit 132 on the head unit 128. In some embodiments, if the occupant 106 had previously created an occupant profile which is stored within the occupant repository 142, the computing device 104 may query the occupant repository 142 to retrieve user identification information that may be utilized to subjectively associate one or more determined anxiety levels to the occupant 106. Upon identifying the occupant 106 based on retrieval of the occupant profile associated with the occupant 106, the computing device 104 may utilize one or more of the plurality of sensors 108, 112, 116, 120 to determine if the occupant 106 seated within the seat 110 has changed to a different individual based on a change of the occupant's weight, disposition within the seat 110, outward extension amount of the seat belt 114, and/or position of the feet of the occupant 106 on the floor board 122 that may be sensed over a predetermined delta threshold (value(s)). In another embodiment, one or more of the cameras 138 may be utilized to capture images of the occupant 106 to determine if the occupant 106 seated within the seat 110 has changed to a different individual based on the execution of machine vision.

In one embodiment, if the occupant 106 seated within the seat 110 is determined to have changed, the computing device 104 may prompt the (different) occupant 106 to identify themselves through the occupant identification user interface presented through the display unit 132 on the head unit 128. In one or more embodiments, if the particular occupant 106 or a previously detected occupant is not detected based on the execution of machine vision by one or more cameras 138, the computing device 104 may utilize the occupant setup user interface to setup an occupant profile to provide user identification information that may be utilized to subjectively associate one or more determined anxiety levels to a (new) occupant 106.

In an alternate embodiment, if the occupant 106 is a new passenger of the vehicle 102 and had not previously utilized the occupant setup user interface to setup an occupant profile, the occupant 106 may input a respective user interface icon presented on the occupant identification user interface. The user interface icon may be inputted by the (new) occupant 106 to utilize the occupant setup user interface to setup an occupant profile to provide user identification information that may be utilized to subjectively associate one or more determined anxiety levels to the (new) occupant 106.

Upon the identification of the occupant 106 seated within the seat 110 of the vehicle 102, the signal reception module 146 of the computing device 104 may be configured to access the measurement database 144 stored on the storage unit 130 to thereby query the database 144 to determine if a record has been previously created for the occupant 106 that may be specifically associated with the particular occupant 106. In one embodiment, if the signal reception module 146 determines that a record that is specifically associated with the particular occupant has not been previously created within the measurement database 144, the signal reception module 146 of the computing device 104 may create a record that is associated with the particular occupant 106 seated within the seat 110.

In one embodiment, the record associated with the particular occupant 106 may include data fields (fields) within the measurement database 144 that are further populated with sensor data and associated time stamps that may be further electronically processed by the neural network 124. In some embodiments, the record associated with the particular occupant 106 may include fields that are populated with processed metrics and associated time stamps that may be further electronically analyzed by the neural network 124 to determine an anxiety level of the particular occupant 106.

Figure 4:
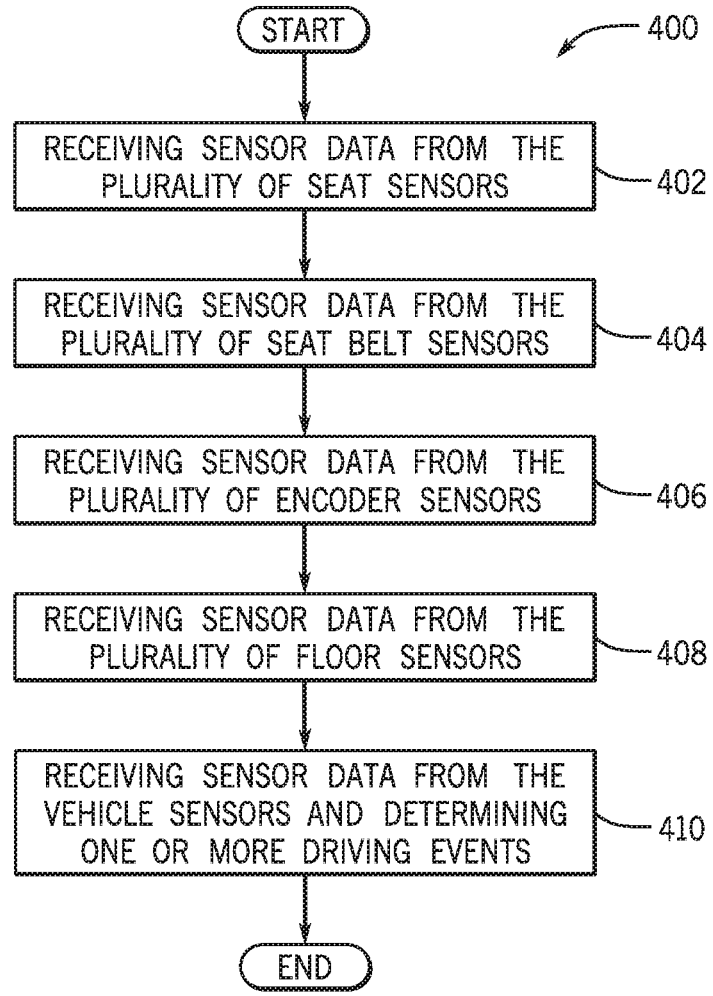
FIG. 4 is a process flow diagram of a method for receiving sensor data from a plurality of sensors and filtering noise from the sensor data according to an exemplary embodiment of the present disclosure.

FIG. 4 is a process flow diagram of a method 400 for receiving sensor data from the plurality of sensors 108, 112, 116, 120 and filtering noise from the sensor data according to an exemplary embodiment of the present disclosure. FIG. 4 will be described with reference to the components of FIG. 1, FIG. 2, and FIG. 3 though it is to be appreciated that the method 400 of FIG. 4 may be used with other systems/components. The method 400 may begin at block 402, wherein the method 400 may include receiving sensor data from the plurality of seat sensors 108.

In an exemplary embodiment, the signal reception module 146 may be configured to communicate with the plurality of seat sensors 108 to send one or more commands to the pressure sensors and the flex sensors of the plurality of seat sensors 108 to receive sensor data. The plurality of seat sensors 108 may responsively send one or more electronic signals that include sensor data in the form of a respective sensor data package (e.g., data package) to the signal reception module 146. As discussed above, the plurality of seat sensors 108 may be configured to sense pressure sensor readings and biometric sensor readings and output the readings pertaining to the occupant 106 seated within the seat 110 as a sensor data package.

In one configuration, upon receiving the one or more electronic sensor signals that include the sensor data package in real-time, the signal reception module 146 may assign a timestamp to the sensor data package that pertains to pressure sensor readings and biometric sensor readings sensed at a particular point in time. In one or more embodiments, the signal reception module 146 may receive numerous sensor data packages for one or more predetermined periods of time (e.g., each 5 seconds). The signal reception module 146 may accordingly communicate the sensor signals that include the numerous sensor data packages to the signal processing module 148 to filter the sensor signals to remove noise artifacts that may be attributed to the movement of the vehicle 102 (e.g., causing noise based on roadway bumps, braking, acceleration, etc.)

In an exemplary embodiment, upon receiving the sensor signals that include each sensor data package, the signal processing module 148 may utilize a Fast Fourier Transform or similar signal processing algorithm to remove noise artifacts from the sensor data package of each of the sensor signals that may be associated with the movement of the vehicle 102. This filtering may be based on machine learning techniques that respond adaptively and may be pre-trained based on certain particular level(s) of filtering that most improve statistical power to remove any potential false positive data during processing of the aggregated sensor data files. In an alternate embodiment, the signal processing module 148 may filter noise artifacts from a sampled evoked biological signal based on the deviations using highly auto-correlated carrier sequence codes (HACS) for example, as discussed in U.S. application Ser. No. 14/961,277, now published as US 2016/0157783, which is expressly incorporated herein by reference.

In another embodiment, one or more of the vehicle sensors 136 may be used in conjunction with one another to provide data regarding movement of the vehicle 102 as the vehicle 102 is being driven on a roadway. For example, vehicle sensors 136 disposed at each wheel of the vehicle 102 may measure a ride level of the vehicle 102 and one or more accelerometers included as part of the vehicle sensors 136 may measure vertical body acceleration of the vehicle 102 in order to accurately measure road noise. The vehicle sensors 136 may also be used to determine the steering angle, roll, pitch, lateral acceleration and yaw of the vehicle 102 as an indication of the vehicle 102 reacting to turns, acceleration, braking, and road noise that may add noise artifacts to each sensor data package included within the one or more electronic sensor signals. Additionally techniques using data from one or more of the vehicle sensors 136 may be utilized to filter noise artifacts from the aggregated sensor data, for example, as discussed in U.S. application Ser. No. 14/697,593, now published as US 2015/0229341, which is expressly incorporated herein by reference.

In an exemplary embodiment, upon filtering each sensor data package included within the one or more electronic sensor signals to remove noise artifacts, the signal processing module 148 may thereby pool and aggregate the filtered sensor data from numerous sensor data packages received for the predetermined period(s) of time to thereby be aggregated. Upon pooling and aggregating the filtered sensor data, the signal processing module 148 may access the measurement database 144 on the storage unit 130 and may query the database for the record associated with the occupant 106.

Upon retrieving the record associated with the occupant 106, the signal processing module 148 may create a field associated with the aggregated (filtered) sensor data package that includes aggregated sensor data received from the plurality of seat sensors 108 for the predetermined period(s) of time and filtered by the signal processing module 148. The signal processing module 148 may thereby populate the respective field with the aggregated sensor data and associated time stamps that indicate the time at which each sensed value included within the sensor data was sensed (captured) by the plurality of seat sensors 108.

Accordingly, the signal processing module 148 may continually receive one or more sensor signals containing sensor data packages for additional predetermined periods of time that may be filtered to remove noise artifacts, pooled, aggregated, and populated within the measurement database 144 as respective aggregated sensor data from the plurality of seat sensors 108 for respective predetermined periods of time. Additionally, the signal reception module 146 may be configured to create numerous additional fields within the record associated with the occupant 106 within the measurement database 144 that may be utilized to store aggregated sensor data sensed (based on the occupant 106 being seated in seat 110) and associated time stamps sensed for each respective predetermined period of time.

The method 400 may proceed to block 404, wherein the method 400 may include receiving sensor data from the plurality of seat belt sensors 112. In an exemplary embodiment, the signal reception module 146 may be configured to communicate with the plurality of seat belt sensors 112 to send one or more commands to the pressure sensors and the flex sensors of the plurality of seat belt sensors 112 to receive sensor data. The plurality of seat belt sensors 112 may responsively send one or more electronic signals that include sensor data in the form of a respective sensor data package to the signal reception module 146. As discussed above, the plurality of seat belt sensors 112 may be configured to sense biometric sensor reading and output the readings pertaining to the occupant 106 seated within the seat 110.

In one configuration, upon receiving the one or more electronic sensor signals that include the sensor data package in real-time, the signal reception module 146 may assign a timestamp to the sensor data package that pertains to pressure sensor readings sensed at a particular point in time. In one or more embodiments, the signal reception module 146 may receive numerous sensor data packages for a predetermined period(s) of time. The signal reception module 146 may accordingly communicate the sensor signals that include the numerous sensor data packages to the signal processing module 148 to filter the sensor signals to remove noise artifacts that may be attributed to the movement of the vehicle 102 (e.g., causing noise based on roadway bumps, braking, acceleration, etc.). The signal processing module 148 may utilize one or more noise filtering processes (discussed above with respect to block 402) to remove noise artifacts from the data package of each of the sensor signals that may be associated with the movement of the vehicle 102.

In an exemplary embodiment, upon filtering each sensor data package included within the one or more electronic sensor signals to remove noise artifacts, the signal processing module 148 may thereby pool the filtered sensor data from numerous sensor data packages received for the predetermined period(s) of time to thereby be aggregated. Upon pooling and aggregating the filtered sensor data, the signal processing module 148 may access the measurement database 144 on the storage unit 130 and may query the database for the record associated with the occupant 106.

Upon retrieving the record associated with the occupant 106, the signal processing module 148 may create a field associated with the aggregated (filtered) sensor data package that includes aggregated sensor data received from the plurality of seat belt sensors 112 for the predetermined period(s) of time and filtered by the signal processing module 148. The signal processing module 148 may thereby populate the respective field with the aggregated sensor data and associated time stamps that indicate the time at which each sensed value included within the sensor data was sensed (captured) by the plurality of seat belt sensors 112.

Accordingly, the signal processing module 148 may continually receive one or more sensor signals containing sensor data packages for additional predetermined periods of time that may be filtered to remove noise artifacts, pooled, aggregated, and populated within the measurement database 144 as respective aggregated sensor data from the plurality of seat belt sensors 112 for respective predetermined periods of time. Additionally, the signal reception module 146 may be configured to create numerous additional fields within the record associated with the occupant 106 within the measurement database 144 that may be utilized to store aggregated sensor data sensed (based on the occupant 106 being seated in seat 110) and associated time stamps sensed for each respective predetermined period of time.

The method 400 may proceed to block 406, wherein the method 400 may include receiving sensor data from the plurality of encoder sensors 116. In an exemplary embodiment, the signal reception module 146 may be configured to communicate with the plurality of encoder sensors 116 of the encoder 118 to send one or more commands to the flex sensors of the plurality of encoder sensors 116 to receive sensor data. The plurality of encoder sensors 116 may responsively output readings pertaining to a number of forward rotations and/or backward rotations of a pin of the retractor or seat belt winding mechanism to thereby capture a frequency and amount of outward rolling or retraction of the seat belt 114 caused by the occupant 106 seated within the seat 110. This may indicate a level of stress placed on the seat belt 114 and may output respective measurements as sensor data in the form of a sensor data package.

In one configuration, upon receiving the one or more electronic sensor signals that include the sensor data package in real-time, the signal reception module 146 may assign a timestamp to the sensor data package that pertains to pressure sensor readings sensed at a particular point in time. In one or more embodiments, the signal reception module 146 may receive numerous sensor data packages for a predetermined period(s) of time. The signal reception module 146 may accordingly communicate the sensor signals that include the numerous sensor data packages to the signal processing module 148 to filter the sensor signals to remove noise artifacts that may be attributed to the movement of the vehicle 102 (e.g., causing noise based on roadway bumps, braking, acceleration, etc.). The signal processing module 148 may utilize one or more noise filtering processes (discussed above with respect to block 402) to remove noise artifacts from the data package of each of the sensor signals that may be associated with the movement of the vehicle 102.

In an exemplary embodiment, upon filtering each sensor data package included within the one or more electronic sensor signals to remove noise artifacts, the signal processing module 148 may thereby pool the filtered sensor data from numerous sensor data packages received for the predetermined period(s) of time to thereby be aggregated. Upon pooling and aggregating the filtered sensor data, the signal processing module 148 may access the measurement database 144 on the storage unit 130 and may query the database for the record associated with the occupant 106.

Upon retrieving the record associated with the occupant 106, the signal processing module 148 may create a field associated with the aggregated (filtered) sensor data package that includes aggregated sensor data received from the plurality of encoder sensors 116 for the predetermined period(s) of time and filtered by the signal processing module 148. The signal processing module 148 may thereby populate the respective field with the aggregated sensor data and associated time stamps that indicate the time at which each sensed value included within the sensor data was sensed (captured) by the plurality of encoder sensors 116.

Accordingly, the signal processing module 148 may continually receive one or more sensor signals containing sensor data packages for additional predetermined periods of time that may be filtered to remove noise artifacts, pooled, aggregated, and populated within the measurement database 144 as respective aggregated sensor data from the plurality of encoder sensors 116 for respective predetermined periods of time. Additionally, the signal reception module 146 may be configured to create numerous additional fields within the record associated with the occupant 106 within the measurement database 144 that may be utilized to store aggregated sensor data sensed (based on the occupant 106 being seated in seat 110) and associated time stamps sensed for each respective predetermined period of time.

The method 400 may proceed to block 408, wherein the method 400 may include receiving the sensor data from the plurality of floor sensors 120. In an exemplary embodiment, the signal reception module 146 may be configured to communicate with the plurality of floor sensors 120 to send one or more commands to the pressure sensors of the plurality of floor sensors 120 to receive sensor data. The plurality of floor sensors 120 may responsively send one or more electronic signals that include sensor data in the form of a respective sensor data package (e.g., data package) to the signal reception module 146. As discussed above, the plurality of floor sensors 120 may be configured to sense pressure sensor readings and output the readings pertaining to the force of the occupant's feet upon the floor board 122 of the vehicle 102 as a sensor data package.

In one configuration, upon receiving the one or more electronic sensor signals that include the sensor data package in real-time, the signal reception module 146 may assign a timestamp to the sensor data package that pertains to pressure sensor readings sensed at a particular point in time. In one or more embodiments, the signal reception module 146 may receive numerous sensor data packages for a predetermined period(s) of time. The signal reception module 146 may accordingly communicate the sensor signals that include the numerous sensor data packages to the signal processing module 148 to filter the sensor signals to remove noise artifacts that may be attributed to the movement of the vehicle 102 (e.g., causing noise based on roadway bumps, braking, acceleration, etc.). The signal processing module 148 may utilize one or more noise filtering processes (discussed above with respect to block 402) to remove noise artifacts from the data package of each of the sensor signals that may be associated with the movement of the vehicle 102.

In an exemplary embodiment, upon filtering each sensor data package included within the one or more electronic sensor signals to remove noise artifacts, the signal processing module 148 may thereby pool the filtered sensor data from numerous sensor data packages received for the predetermined period(s) of time to thereby be aggregated. Upon pooling and aggregating the filtered sensor data, the signal processing module 148 may access the measurement database 144 on the storage unit 130 and may query the database for the record associated with the occupant 106.

Upon retrieving the record associated with the occupant 106, the signal processing module 148 may create a field associated with the aggregated (filtered) sensor data package that includes aggregated sensor data received from the plurality of floor sensors 120 for the predetermined period(s) of time and filtered by the signal processing module 148. The signal processing module 148 may thereby populate the respective field with the aggregated sensor data and associated time stamps that indicate the time at which each sensed value included within the sensor data was sensed (captured) by the plurality of floor sensors 120.

Accordingly, the signal processing module 148 may continually receive one or more sensor signals containing sensor data packages for additional predetermined periods of time that may be filtered to remove noise artifacts, pooled, aggregated and populated within the measurement database 144 as respective aggregated sensor data from the plurality of floor sensors 120 for respective predetermined periods of time. Additionally, the signal reception module 146 may be configured to create numerous additional fields within the record associated with the occupant 106 within the measurement database 144 that may be utilized to store aggregated sensor data sensed (based on the occupant 106 being seated in seat 110) and associated time stamps sensed for each respective predetermined period of time.

The method 400 may proceed to block 410, wherein the method 400 may include receiving sensor data from the vehicle sensors 136 and determining one or more driving events that occur simultaneously to the sensing of data by the plurality of sensors 108, 112, 116, 120. In one embodiment, one or more driving events that simultaneously take place when sensor readings are captured by the plurality of sensors 108, 112, 116, 120 may be determined.

In particular, the one or more driving events may be determined based on the utilization of the vehicle sensors 136. The signal reception module 146 may be configured to receive sensor data from the vehicle sensors 136 pertaining to the surrounding environment of the vehicle 102. Upon continually receiving sensor data from the vehicle sensors 136 as the vehicle 102 is being operated, the signal reception module 146 may communicate respective sensor data packages for the predetermined period(s) of time to the signal processing module 148 of the computing device 104.

In one embodiment, upon receiving the sensor data packages, the signal processing module 148 may be configured to execute computer logic to aggregate sensor data included within the sensor data packages from the (various) vehicle sensors 136 and determine one or more driving events that occur at particular points in time. The driving events may include one or more driving conditions that may occur within a surrounding environment of the vehicle 102 that may affect how the vehicle 102 is operated, the characteristics of one or more roadways including the roadway on which the vehicle 102 is traveling, one or more traffic signals, and one or more traffic signs that may also affect how the vehicle 102 is driven/operated. The one or more driving events may additionally include one or more vehicle dynamics associated with how the vehicle 102 is operated based on the characteristics of one or more roadways including the roadway on which the vehicle 102 is traveling, one or more traffic signals, and one or more traffic signs that may also affect how the vehicle 102 is driven/operated.

In one embodiment, upon determining one or more driving events, the signal processing module 148 may compute time stamps associated with the one or more driving events. The timestamps may include a time(s)/timeframe(s) at which each of the one or more driving events take place during the predetermined period(s) of time for which the sensor data from the plurality of sensors 108, 112, 116, 120 is aggregated (as discussed above with respect to blocks 402-408). Upon computing the time stamps that are associated with each of the one or more driving events, the signal processing module 148 may access the measurement database 144 and query the fields of the record associated with the occupant 106 to determine aggregated sensor data sensed by one or more of the plurality of sensors 108, 112, 116, 120 that may include a matching time stamp. In other words, the signal processing module 148 may query the measurement database 144 to determine one or more fields that include aggregated sensor data that was sensed/captured at the same time as when one or more of the driving events took place.

In one configuration, upon querying the fields of the record associated with the occupant 106 within the measurement database 144, if the signal processing module 148 determines that aggregated sensor data from one or more of the plurality of sensors 108, 112, 116, 120 is stored within one or more fields, the module 148 may access the respective fields and add data pertaining to the one or more driving events that include a matching time stamp. Accordingly, the aggregated sensor data may be stored within a particular field with data that pertains to one or more driving events that simultaneously take place as when the sensor data is captured by one or more of the plurality of sensors 108, 112, 116, 120.

As an illustrative embodiment, if the plurality of seat sensors 108 sense pressure sensing values and biometric sensing values which are aggregated and stored within a particular field with a particular time stamp (1:36), the signal processing module 148 may store data pertaining to one or more driving events that may have taken place simultaneously (at 1:36). This functionality may ensure that aggregated sensor data that specifically pertains to the occupant 106 is paired with one or more driving events which may affect how the vehicle 102 is driven/operated.

Figure 5:
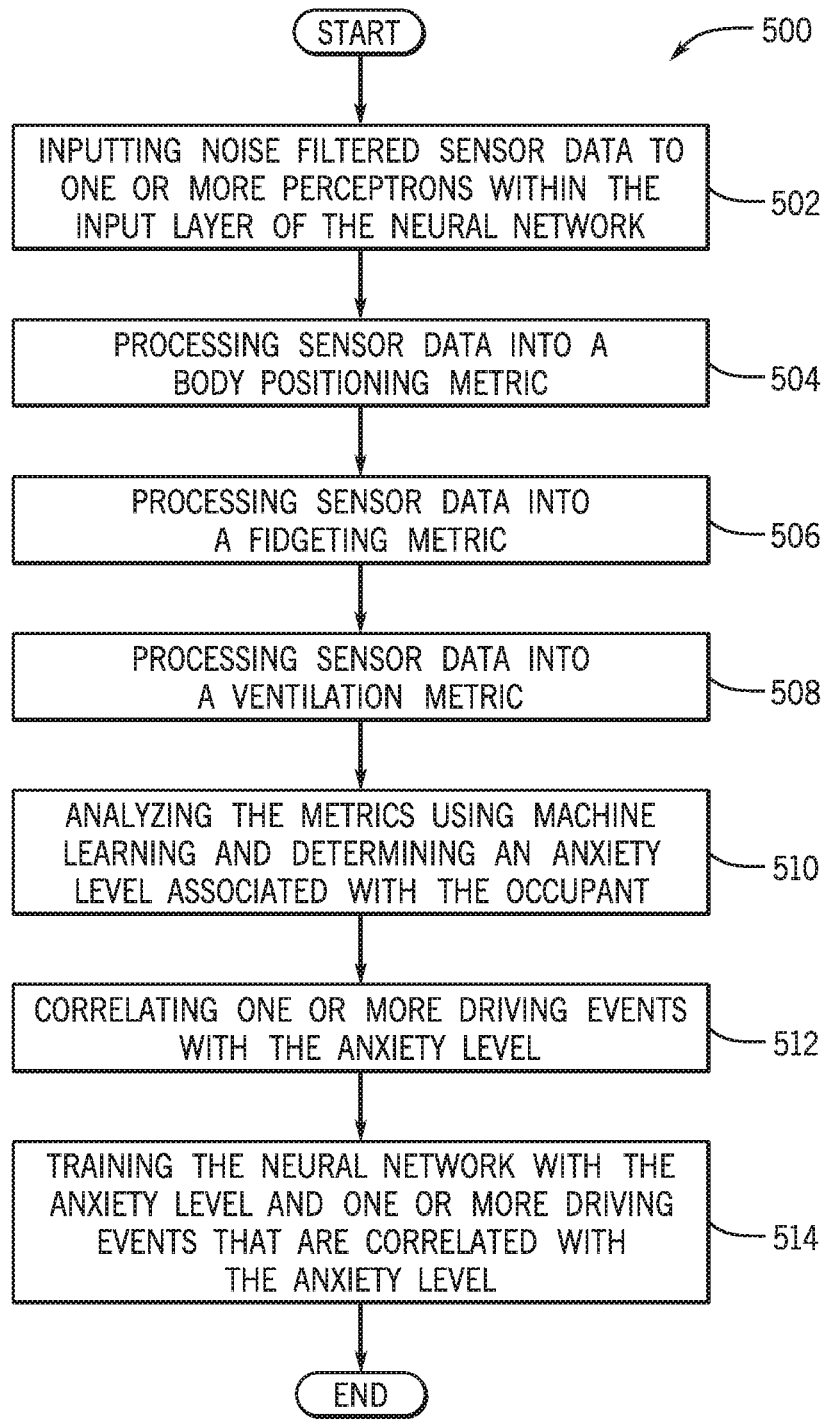
FIG. 5 is a process flow diagram of a method for processing the sensor data into metrics associated with a type of measurement and analyzing the processed metrics to determine an anxiety level associated with an occupant of the vehicle according to an exemplary embodiment of the present disclosure.

FIG. 5 is a process flow diagram of a method 500 for processing the sensor data into metrics associated with a type of measurement and analyzing the processed metrics to determine an anxiety level associated with the occupant 106 of the vehicle 102 according to an exemplary embodiment of the present disclosure. FIG. 5 will be described with reference to the components of FIG. 1, FIG. 2, and FIG. 3 though it is to be appreciated that the method 500 of FIG. 5 may be used with other systems/components. The method 500 may begin at block 502, wherein the method 500 may include inputting noise filtered sensor data to one or more perceptrons 316 within the input layer 302 of the neural network 124.

In an exemplary embodiment, the signal processing module 148 may be configured to access the measurement database 144 on the storage unit 130 and may query the record associated with the occupant 106 to retrieve the filtered aggregated sensor data previously populated at blocks 402-408. Upon retrieving the filtered aggregated sensor data provided based on sensing for the predetermined period(s) of time by the plurality of seat sensors 108, the plurality of seat belt sensors 112, the plurality of encoder sensors 116, and the plurality of floor sensors 120, the signal processing module 148 may input the sensor data to the neural network 124. In particular, the signal processing module 148 may input the sensor data retrieved from the respective fields of the record associated with the occupant 106 of the measurement database 144 to the input layer 302 of the neural network 124 to be evaluated and processed by the perceptrons 316 of the neural network 124.

The method 500 may proceed to block 504, wherein the method 500 may include processing sensor data into a body positioning metric. In an exemplary embodiment, upon being received by the input layer 302, the sensor data associated with filtered aggregated sensor data provided based on sensing for the predetermined period(s) of time by the plurality of seat sensors 108, the plurality of seat belt sensors 112, the plurality of encoder sensors 116, and the plurality of floor sensors 120 may be further provided to the digital signal processing layer 304 and/or hidden layers 306-310 for the perceptrons 316 of the respective layers to complete DSP that may utilize information based on the pre-training of the neural network 124 (discussed above).

In an exemplary embodiment, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of seat sensors 108. In one embodiment, the noise filtered sensor data pertaining to flex and pressure sensor readings for the predetermined period(s) of time (e.g., 5 seconds) may be evaluated to determine pressure that may be applied to various portions of the seat 110 and/or biometric readings (e.g., body heat) that may be applied to various portions of the seat 110 for period(s) of time to process a metric value that may pertain to the body position of the occupant 106 within the seat 110. The metric value may be processed based on pre-trained data that may indicate an amount of stress and tension that may be exhibited based on the sensed body position of the occupant 106 based on the seating posture of the occupant 106 and/or biometric data as sensed within the seat 110.

As an illustrative example, if the occupant 106 is determined to be seated with their back rested against the seat back of the seat 110 in a calm manner, a metric value (e.g., 3/10) may be processed that indicates a calm/non-stressed body posture. Alternatively, if the occupant 106 is determined to be seated with tense and hunched body position for one or more periods of time, a metric value (e.g., 9/10) may be processed that may also be based on the length of time of the body position or changes in the body position of the occupant 106 over one or more predetermined periods of time. In other words, body positions within the seat that indicate less stress and tension of the occupant 106 may be processed as lower metric values whereas body positions within the seat that indicate higher stress and tension of the occupant 106 may be processed as higher metric values.

Additionally, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of floor sensors 120. In one embodiment, the noise filtered sensor data pertaining to pressure sensor readings for the predetermined period(s) of time may be evaluated to determine pressure that may be applied to various portions of the floor board 122 for period(s) of time to process a metric value that may pertain to the body position of the occupant 106 with respect to sensing by the plurality of floor sensors 120. The metric value may be associated with pre-trained data that may indicate an amount of stress and tension that may be exhibited based on the sensed body position of the occupant 106 based on the pressure (force) applied to the floor board 122 for one or more periods of time.

As an illustrative example, if the occupant 106 is determined to be applying little downward pressure from their feet upon the floor board 122 of the vehicle 102 for one or more periods of time, a metric value (e.g., 2/10) may be processed that indicates a calm/non-stressed body posture. Alternatively, if the occupant 106 is determined to be applying a high amount of pressure for one or more periods of time, a metric value (9/10) may be processed that may also be based on the length of time of the body position or changes in the body position of the occupant 106 over one or more predetermined periods of time. In other words, a body position that includes a lower amount of foot pressure on the floor board 122 that indicates less stress and tension of the occupant 106 may be processed with lower metric values whereas a body position that includes a higher amount of foot pressure within the seat 110 that indicates higher stress and tension of the occupant 106 may be processed with higher metric values.

In one or more embodiments, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of seat belt sensors 112. In one embodiment, the noise filtered sensor data pertaining to flex and pressure sensor readings for the predetermined period(s) of time (e.g., 5 seconds) may be evaluated to determine pressure that may be applied to various portions of the seat belt 114 and/or biometric readings (e.g., body heat) that may be sensed at various portions of the seat belt 114 for period(s) of time to process a metric value that may pertain to the body position of the occupant 106 based on sensed data by the plurality of seat belt sensors 112. The metric value may be associated with pre-trained data that may indicate an amount of stress and tension that may be exhibited based on the sensed body position of the occupant 106 based on the seating posture of the occupant 106 and/or biometric data that may be indicated based on the occupant 106 contacting one or more portions of the seat belt 114.

As an illustrative example, if the occupant 106 is determined to be seated in a calm manner based on a low amount of pressure placed upon a top portion of the seat belt 114, a metric value (e.g., 3/10) may be processed that indicates a calm/non-stressed body posture. Alternatively, if the occupant 106 is determined to be seated with tense and hunched body position for one or more periods of time based on a high amount of pressure that is placed upon a top portion of the seat belt 114, a metric value (e.g., 9/10) may be processed that may also be based on the length of time of the body position or changes in the body position of the occupant 106 over one or more predetermined periods of time. In other words, body positions that may be indicated based on the occupant 106 contacting one or more portions of the seat belt 114 that indicate less stress and tension of the occupant 106 may be processed as lower metric values whereas body positions that may be indicated based on the occupant 106 contacting one or more portions of the seat belt 114 that indicate higher stress and tension of the occupant 106 may be processed as higher metric values.

In one embodiment, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of encoder sensors 116 of the encoder 118 attached to the roller of the seat belt 114. In one embodiment, the noise filtered sensor data pertains to a number of forward rotations and/or backward rotations of the pin that is attached to the roller to rotate the seat belt 114 to thereby capture a frequency and amount of outward rolling or retraction of the seat belt 114 caused by the occupant 106 seated within the seat 110 for the predetermined period(s) of time. This data may be evaluated to determine an amount(s) of extension or retraction of the seat belt 114 for period(s) of time to process a metric value that may pertain to the body position of the occupant 106 based on sensed data provided by the plurality of encoder sensors 116. The metric value may be associated with pre-trained data that may indicate an amount of stress and tension that may be exhibited based on the sensed body position of the occupant 106 based on the frequency and amount of extension or retraction of the seat belt 114 for one or more predetermined periods of time.

As an illustrative example, if the occupant 106 is determined to be applying less movement which would extend and/or retract the seat belt 114 for one or more periods of time, a metric value (e.g., 3/10) may be processed that indicates a calm/non-stressed body posture. Alternatively, if the occupant 106 is determined to be applying more (high amount of) movement which would extend and/or retract the seat belt 114 at a high frequency and high amount (of rotations of the pin) for one or more periods of time, a metric value (9/10) may be processed that may also be based on the length of time of the body position or changes in the body position of the occupant 106 over one or more predetermined periods of time. Such a high amount and/or frequency of extension and/or retraction of the seat belt 114 as determined based on the high amount and/or frequency of the rotation of the pin may indicate that the occupant 106 may be hunching over and/or tense. In other words, a body position that includes lower amount and/or frequency of extension and/or retraction on the seat belt 114 indicates less stress and tension of the occupant 106 and may be processed as lower metric values whereas a body position that includes a higher amount and/or frequency of extension and/or retraction on the seat belt 114 indicates higher stress and tension of the occupant 106 and may be processed as higher metric values.

In an exemplary embodiment, upon processing the four aforementioned metric values pertaining to the body position of the occupant 106, based on sensing for the predetermined period(s) of time by the plurality of sensors 108, 112, 116, 120, the perceptrons 316 of the neural network 124 may apply weighting to each of the metric values that may be based on the pre-trained data. Such weighting may be applied to indicate an amount of impact that each metric value associated with respective sensed data provided by the plurality of sensors 108, 112, 116, 120 may have in processing a body position metric associated with the body position of the occupant 106 (which brings sensor data provided by all of the plurality of sensors 108, 112, 116, 120 together).

Upon weighting of the four metric values into four weighted (e.g., adjusted) metric values, the perceptrons 316 of the neural network 124 may aggregate the four weighted values into the body position metric which may indicate a level of anxiety that may be associated with the body position of the occupant 106 as determined based on the sensed data provided in aggregate by the plurality of sensors 108, 112, 116, 120. In one embodiment, the body position metric may be inputted to the perceptron(s) 316 of the output layer to be further evaluated to determine and output the anxiety level of the occupant 106.

The method 500 may proceed to block 506, wherein the method 500 may include processing sensor data into a fidgeting metric. In an exemplary embodiment, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of seat sensors 108.

In one embodiment, the noise filtered sensor data pertaining to pressure sensor readings for the predetermined period(s) of time (e.g., 5 seconds) may be evaluated to determine a change in pressure distribution that may be applied to various portions of the seat 110 for a period(s) of time to process a metric value that may pertain to the level of fidgeting exhibited by the occupant 106 within the seat 110. The metric value may be processed based on pre-trained data that may indicate an amount and/or frequency of fidgeting that may be exhibited based on rapid changes or deltas in the sensed body movement of the occupant 106 within the seat 110. In particular, the perceptrons 316 may determine a number of fluctuations in pressure values (that indicates a change in pressure distribution on the seat 110) over one or more predetermined periods of time that may provide an indication of a level of fidgeting and in turn an amount of stress and tension of the occupant 106 seated within the seat 110.

As an illustrative example, if a low amount of fluctuations in pressure values are sensed over one or more periods of time based on a low amount of body movement of the occupant 106 seated within the seat 110, a metric value (e.g., 3/10) may be processed that indicates little to no fidgeting that may pertain to calm/non-stressed body movements. Alternatively, if a high amount of fluctuations in pressure values are sensed over one or more periods of time, a metric value (e.g., 9/10) may be processed that indicates fidgeting that may be determined based on a high amount of change in the movement of the body of the occupant 106 over one or more predetermined periods of time. In other words, the change in the body movement of the occupant 106 that indicates little or no fidgeting may be processed as lower metric values whereas the change in the body movement of the occupant 106 that indicates more or a high amount of fidgeting may be processed as higher metric values.

Additionally, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of floor sensors 120. In one embodiment, the noise filtered sensor data pertaining to pressure sensor readings for the predetermined period(s) of time may be evaluated to determine one or more spikes in foot pressure in one or more predetermined periods of time to process a metric value that may pertain to the level of fidgeting exhibited by the occupant 106.

In particular, the metric value may be associated with pre-trained data that may indicate an amount of stress and tension that may be exhibited based on a rate of foot tapping over one or more predetermined periods of time exhibited by the occupant 106 based on the force applied to the floor board 122 that may include an amount of fidgeting exhibited by the occupant 106 over the course of one or more predetermined periods of time. In other words, the metric value may be indicative of an amount of stress and tension that may be exhibited by the occupant 106 over one or more predetermined periods of time as compared to a predetermined amount which is expected of the occupant 106 in a non-tense/non-stressed state (as pre-trained to the neural network 124).

As an illustrative example, if the occupant 106 is determined to be applying a low rate of foot tapping upon the floor board 122 of the vehicle 102 for one or more periods of time, based on the sensing of little or no spikes in pressure by the plurality of floor sensors 120, a metric value (e.g., 2/10) may be processed that indicates little to no fidgeting expressed by the occupant 106. Alternatively, if the occupant 106 is determined to be applying a high rate of foot tapping upon the floor board 122 of the vehicle 102 for one or more periods of time, based on the sensing of many spikes in pressure sensed by the plurality of floor sensors 120, a metric value (9/10) may be processed indicating a high level of fidgeting expressed by the occupant 106. The metric value may also be based on the length of time of the fidgeting or changes in the fidgeting of the occupant 106 over one or more predetermined periods of time. In other words, a lower level of fidgeting over one or more predetermined periods of time may indicate less stress and tension of the occupant 106 and may be processed with lower metric values whereas a higher level of fidgeting over one or more predetermined periods of time may indicate higher stress and tension of the occupant 106 and may be processed with higher metric values.

In one or more embodiments, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of seat belt sensors 112. In one embodiment, the noise filtered sensor data pertaining to pressure sensor readings for the predetermined period(s) of time may be evaluated to determine pressure that may be applied to various portions of the seat belt 114 for period(s) of time to process a metric value that may pertain to the level of fidgeting exhibited by the occupant 106 within the seat 110.

The metric value may be processed based on pre-trained data that may indicate an amount of fidgeting that may be exhibited based on rapid changes or deltas in the sensed body movement of the occupant 106 based on sensed data by the plurality of seat belt sensors 112. In particular, the perceptrons 316 may determine a number of fluctuations in pressure values over one or more predetermined periods of time that may provide an indication of a level of fidgeting and in turn an amount of stress and tension of the occupant 106 that may be indicated based on the occupant 106 contacting one or more portions of the seat belt 114.

As an illustrative example, if a low amount of fluctuations in pressure values are sensed over one or more periods of time based on a low amount of body movement of the occupant 106 as sensed by the occupant 106 contacting one or more portions of the seat belt 114, a metric value (e.g., 3/10) may be processed that indicates little to no fidgeting that may pertain to calm/non-stressed body movements. Alternatively, if a high amount of fluctuations in pressure values are sensed over one or more periods of time as sensed by the occupant 106 contacting one or more portions of the seat belt 114, a metric value (e.g., 9/10) may be processed that indicates fidgeting that may be determined based on a high amount of change in the movement of the body of the occupant 106 over one or more predetermined periods of time. In other words, the change in the body movement of the occupant 106 based on the occupant 106 contacting one or more portions of the seat belt 114 that indicates little or no fidgeting may be processed as lower metric values whereas the change in the body movement of the occupant 106 based on the occupant 106 contacting one or more portions of the seat belt 114 that indicates more or a high amount of fidgeting may be processed as higher metric values.

In one embodiment, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of encoder sensors 116 of the encoder 118. In one embodiment, the noise filtered sensor data is based on the sensing of forward rotations and/or backward rotations of the pin that is attached to the roller to rotate the seat belt 114.

This data may be evaluated to determine a frequency, speed, and/or an amount of extension or retraction of the seat belt 114 for period(s) of time to process a metric value that may pertain to fidgeting exhibited by the occupant 106 based on sensed data provided by the plurality of encoder sensors 116. The metric value may be associated with pre-trained data that may indicate an amount of stress and tension that may be exhibited due to frequent and/or vigorous movement of the body of the occupant 106 that may be indicated by the frequency, speed, and amount of extension or retraction of the seat belt 114 that may occur over one or more predetermined periods of time.

As an illustrative example, if the occupant 106 is determined to be moving less frequently and/or vigorously which would cause a lower frequency, speed, and amount of extension and/or retraction of the seat belt 114 for one or more periods of time, a metric value (e.g., 3/10) may be processed that indicates little amount of fidgeting. Alternatively, if the occupant 106 is determined to be moving more frequently and/or vigorously which would cause a higher frequency, speed, and/or amount of extension and/or retraction of the seat belt 114 for one or more periods of time, a metric value (9/10) may be processed that may also be based on the length of time of one or more frequent and/or vigorous movements by the occupant 106 over one or more predetermined periods of time. Such a high frequency, speed, and/or amount of extension and/or retraction of the seat belt 114 as determined based on the high amount and/or frequency of the rotation of the pin may indicate that the occupant 106 may be moving in an excited manner which may cause rapid changes is the movement of the upper portion of the occupant's body which may influence the movement of the seat belt 114.

In an exemplary embodiment, upon processing the four aforementioned metric values associated with a level of fidgeting exhibited by the occupant 106, based on sensing for the predetermined period(s) of time by the plurality of sensors 108, 112, 116, 120, the perceptrons 316 of the neural network 124 may apply weighting to each of the metric values that may be based on the pre-trained data. Such weighting may be applied to indicate an amount of impact that each metric value associated with respective sensed data provided by the plurality of sensors 108, 112, 116, 120 may have in processing the fidgeting metric associated with the level of fidgeting exhibited by the occupant 106 (which brings sensor data provided by all of the plurality of sensors 108, 112, 116, 120 together).

Upon weighting of the four metric values into four weighted (e.g., adjusted) metric values, the perceptrons 316 of the neural network 124 may aggregate the four weighted values into the fidgeting metric which may indicate a level of anxiety that may be associated with the movement of the occupant 106 as determined based on the sensed data provided in aggregate by the plurality of sensors 108, 112, 116, 120. In one embodiment, the fidgeting metric may be inputted to the perceptron(s) 316 of the output layer to be further evaluated to determine and output the anxiety level of the occupant 106.

The method 500 may proceed to block 508, wherein the method 500 may include processing sensor data into a ventilation metric. In an exemplary embodiment, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of seat sensors 108. In one embodiment, the noise filtered sensor data pertaining to flex sensor readings for the predetermined period(s) of time (e.g., 5 seconds) may be evaluated to determine a breathing rate (based on contraction of lungs, heart rate, pulse), as sensed by the flex sensors of the plurality of seat sensors 108 for period(s) of time to process a metric value that may pertain to the ventilation rate exhibited by the occupant 106 within the seat 110.

The metric value may be processed based on pre-trained data that may indicate an amount and/or frequency of ventilation that may be exhibited based on rapid changes or deltas in a breathing rate of the occupant 106 within the seat 110. In particular, the perceptrons 316 may determine a number of fluctuations in the breathing rate of the occupant 106 over one or more predetermined periods of time which may provide an indication of a ventilation rate (e.g., hyperventilation) exhibited by the occupant 106 and in turn an amount of stress and tension of the occupant 106 seated within the seat 110.

As an illustrative example, if a low amount of fluctuations in the breathing rate of the occupant 106 are sensed over one or more periods of time based on an average/normal (e.g., based on pre-trained data) of the occupant 106 seated within the seat 110, a metric value (e.g., 4/10) may be processed that indicates a semi-normal ventilation rate exhibited by the occupant 106 that may pertain to a calm/non-anxious state. Alternatively, if a high amount of fluctuations in breathing rate of the occupant 106 are sensed over one or more periods of time, a metric value (e.g., 9/10) may be processed that indicates a high ventilation rate exhibited by the occupant caused by a stressed/anxious state. In other words, the change in the breathing rate of the occupant 106 that indicates a normal breathing rate may be processed as lower metric values whereas the change in the breathing rate of the occupant 106 that indicates a higher breathing rate that may be associated with hyperventilation exhibited by the occupant 106 may be processed as higher metric values.

In one or more embodiments, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of seat belt sensors 112. In one embodiment, the noise filtered sensor data pertaining to flex sensor readings for the predetermined period(s) of time (e.g., 5 seconds) may be evaluated to determine a breathing rate, as sensed by the flex sensors of plurality of seat belt sensors 112 of the seat belt 114 for period(s) of time to process a metric value that may pertain to the ventilation rate exhibited by the occupant 106 within the seat 110.

The metric value may be processed based on pre-trained data that may indicate an amount and/or frequency of ventilation that may be exhibited based on rapid changes or deltas in a breathing rate of the occupant 106 that may be sensed based on contact against one or more portions of the seat belt 114. In particular, the perceptrons 316 may determine a number of fluctuations in the breathing rate of the occupant 106 over one or more predetermined periods of time which may provide an indication of a ventilation rate (e.g., hyperventilation) exhibited by the occupant 106 and in turn an amount of stress and tension of the occupant 106.

As an illustrative example, if an average/normal amount of fluctuations in the breathing rate of the occupant 106 are sensed over one or more periods of time (e.g., based on pre-trained data) based on the occupant 106 contacting one or more portions of the seat belt 114, a metric value (e.g., 1/10) may be processed that indicates a normal ventilation rate exhibited by the occupant 106 that may pertain to calm/non-anxious state. Alternatively, if a high amount of fluctuations in breathing rate of the occupant 106 are sensed over one or more periods of time as sensed by the occupant 106 contacting one or more portions of the seat belt 114, a metric value (e.g., 9/10) may be processed that indicates a high ventilation rate exhibited by the occupant caused by a stressed/anxious state. In other words, the change in the breathing rate of the occupant 106 that indicates a normal breathing rate may be processed as lower metric values whereas the change in the breathing rate of the occupant 106 that indicates a higher breathing rate that may be associated with hyperventilation exhibited by the occupant 106 may be processed as higher metric values.

Additionally, based on the pre-training of the neural network 124, the perceptrons 316 may utilize machine learning/deep learning to provide artificial intelligence capabilities to evaluate the noise filtered sensor data based on sensing for the predetermined period(s) of time by the plurality of encoder sensors 116 of the encoder 118 attached to the roller of the seat belt 114. In one embodiment, the noise filtered sensor data pertains to a subtle change in forward rotations and/or backward rotations of the pin that is attached to the roller to rotate the seat belt 114. The subtle change in the outward rolling or retraction of the seat belt 114 may be caused by the occupant 106 seated within the seat 110 for the predetermined period(s) of time and may pertain to the breathing rate of the occupant 106 caused by contact of the seat belt 114 with the chest and diaphragm of the occupant 106.

This data may be evaluated to determine a rate of subtle changes in the extension or retraction of the seat belt 114 for period(s) of time to process a metric value that may pertain to the ventilation rate exhibited by the occupant 106 based on sensed data provided by the plurality of encoder sensors 116. In particular, the perceptrons 316 may determine a number of fluctuations in the breathing rate of the occupant 106 over one or more predetermined periods of time which may provide an indication of a ventilation rate (e.g., hyperventilation) exhibited by the occupant 106 and in turn an amount of stress and tension of the occupant 106 based on the rate of subtle changes in the extension or retraction of the seat belt 114 that may occur over the one or more predetermined periods of time.

As an illustrative example, upon evaluation of the subtle changes in the extension or retraction of the seat belt 114 that may occur over the one or more predetermined periods of time, a metric value (e.g., 3/10) may be processed that indicates a lower rate of subtle changes that may pertain to a semi-normal ventilation rate exhibited by the occupant 106 that may pertain to calm/non-anxious state. Alternatively, upon evaluation of the subtle changes in the extension or retraction of the seat belt 114 that may occur over the one or more predetermined periods of time, a metric value (e.g., 9/10) may be processed that indicates a higher rate of subtle changes that may pertain to a high ventilation rate exhibited by the occupant a hyperventilation caused by a stressed/anxious state. In other words, the change in the breathing rate of the occupant 106 based on a lower rate of subtle changes in the extension or retraction of the seat belt 114 that indicates a normal breathing rate may be processed as lower metric values whereas the change in the breathing rate of the occupant 106 based on the higher rate of subtle changes in the extension or retraction of the seat belt 114 that indicates a higher breathing rate that may include hyperventilation may be processed as higher metric values.

In an exemplary embodiment, upon processing the three aforementioned metric values associated with a level of fidgeting exhibited by the occupant 106, based on sensing for the predetermined period(s) of time by the plurality of sensors 108, 112, 116, the perceptrons 316 of the neural network 124 may apply weighting to each of the metric values that may be based on the pre-trained data. Such weighting may be applied to indicate an amount of impact that each metric value associated with respective sensed data provided by the plurality of sensors 108, 112, 116 may have in processing a ventilation metric associated with the level of fidgeting exhibited by the occupant 106 (which brings sensor data provided by all of the plurality of sensors 108, 112, 116 together).

Upon weighting of the three metric values into three weighted (e.g., adjusted) metric values, the perceptrons 316 of the neural network 124 may aggregate the three weighted values into the ventilation metric which may indicate a level of anxiety that may be associated with the ventilation rate of the occupant 106 as determined based on the sensed data provided in aggregate by the plurality of sensors 108, 112, 116. In one embodiment, the ventilation metric may be inputted to the perceptron(s) 316 of the output layer to be further evaluated to determine and output the anxiety level of the occupant 106.

The method 500 may proceed to block 510, wherein the method 500 may include analyzing the metrics using machine learning and determining an anxiety level associated with the occupant 106. In one embodiment, the perceptron(s) 316 of the output layer 312 of the neural network 124 may receive the body position metric (processed at block 504), the fidgeting metric (processed at block 506), and the ventilation metric (processed at block 508).

Upon receipt of the metrics, the neural network 124 may utilize machine learning/deep learning to provide artificial intelligence capabilities to access the measurement database 144 and may create an anxiety dataset metric field that is included within the record that is associated with the occupant 106. The anxiety dataset metric field may be created and populated with the body position metric, the fidgeting metric, and the ventilation metric processed by the neural network 124 to maintain (historic) metrics data that may be evaluated against one or more models to determine one or more anxiety levels of the occupant 106 at various points in time.

The neural network 124 may additionally pass the body position metric, the fidgeting metric, and the ventilation metric through one or more pre-trained data classifiers. The one or more pre-trained data classifiers may be utilized to evaluate each of the values of the body position metric, the fidgeting metric, and the ventilation metric against one or more anxiety level determining models that pertain to a body position of an individual experiencing one or more levels of anxiety, a level of fidgeting of an individual experiencing one or more levels of anxiety, and a ventilation rate of an individual experiencing one or more levels of anxiety.

The pre-trained data classifier(s) may thereby classify and determine a (real-time) anxiety level that is associated with the occupant 106 for one or more predetermined periods of time. In one embodiment, the neural network 124 may thereby output the determined anxiety level of the occupant 106 to the anxiety level output module 150 of the computing device 104. In an alternate embodiment, the pre-trained data classifier(s) may thereby classify and predict an anxiety level that is associated with the occupant 106 for one or more immediate subsequent periods of time based on the pre-trained classifier(s). In one embodiment, the neural network 124 may thereby output the predicted anxiety level of the occupant 106 to the anxiety level output module 150 of the computing device 104.

The method 500 may proceed to block 512, wherein the method 500 may include correlating one or more driving events with the anxiety level. In one embodiment, upon determining and outputting the (real-time) anxiety level of the occupant 106, the anxiety level output module 150 may access the measurement database 144 to query the fields that include the sensor data that was provided by the plurality of sensors 108, 112, 116, 120, filtered, and inputted to the neural network 124 (at block 502). As discussed above (with respect to block 410), the fields that include the data may additionally include data pertaining to the one or more driving events that include a matching time stamp as the time stamp associated with the sensor data. Accordingly, the aggregated sensor data may be stored within a particular field with data that pertains to one or more driving events that simultaneously take place as when the sensor data is captured by one or more of the plurality of sensors 108, 112, 116, 120.

In one embodiment, the anxiety level output module 150 may thereby retrieve the one or more driving events and correlate the one or more driving events to the anxiety level output by the neural network 124. In other words, the correlation of one or more driving events with the determined anxiety level of the occupant 106 may be utilized to thereby determine one or more driving events that may partially cause the particular anxiety level of the occupant 106.

The method 500 may proceed to block 514, wherein the method 500 may include training the neural network 124 with the anxiety level and one or more driving events that are correlated with the anxiety level. In one embodiment, the anxiety level output module 150 may access the anxiety prediction dataset 126 on the storage unit 130. Upon accessing the anxiety prediction dataset 126, the module 150 may add the anxiety level and one or more correlated driving events within the anxiety prediction dataset 126 to thereby train the neural network 124 to predict when the occupant 106 may experience a particular level of anxiety based on the occurrence of one or more similar driving events (that may be occurring in real-time) based on analysis of the dataset 126.

As discussed, in one or more embodiments, the computing device 104 may be configured to present one or more interfaces and/or alerts through the display unit 132 and/or other components of the vehicle 102 based on one or more driving events, determined real-time levels of anxiety associated with the occupant 106, and/or predicted levels of anxiety associated with the occupant 106. In some embodiments, the computing device 104 may communicate one or more commands to the vehicle systems 134 to control one or more of the vehicle systems 134 to provide feedback and/or autonomous or semi-autonomous control of the vehicle 102 based on one or more driving events, determined real-time levels of anxiety associated with the occupant 106, and/or predicted levels of anxiety associated with the occupant 106.

Figure 6:
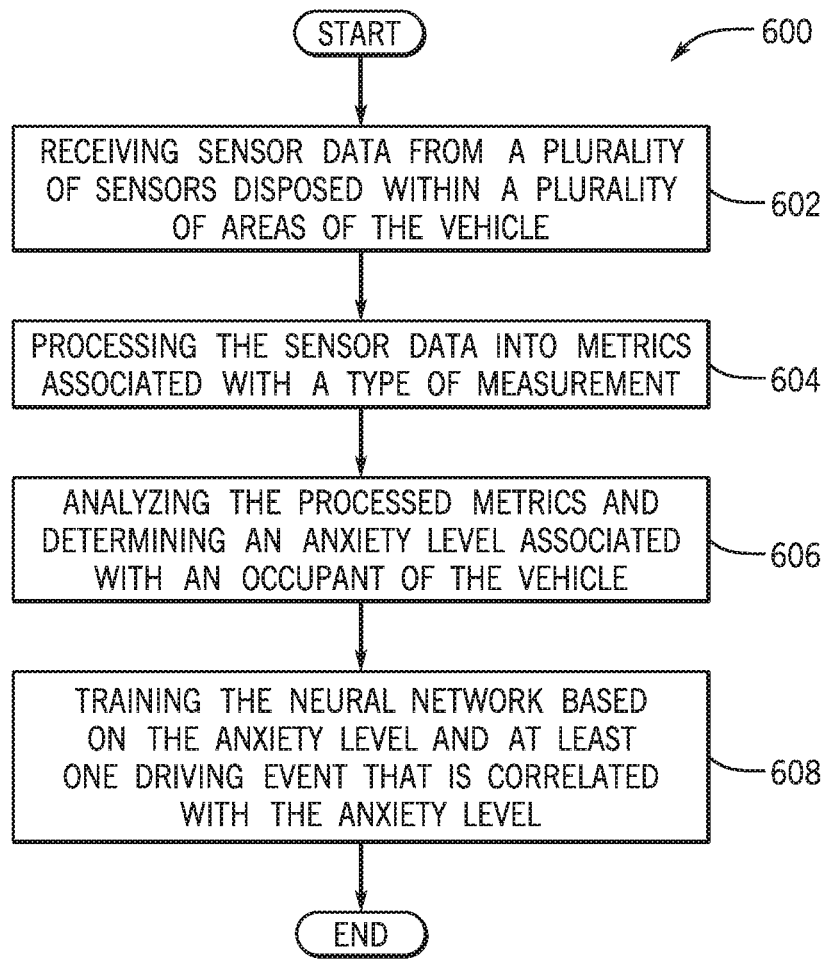
FIG. 6 is a process flow diagram of a method for determining a measurement of occupant anxiety in a vehicle according to an exemplary embodiment of the present disclosure.

FIG. 6 is a process flow diagram of a method 600 for determining a measurement of occupant anxiety in a vehicle 102 according to an exemplary embodiment of the present disclosure. FIG. 6 will be described with reference to the components of FIG. 1, FIG. 2, and FIG. 3 though it is to be appreciated that the method 500 of FIG. 5 may be used with other systems/components. The method 600 may begin at block 602, wherein the method 600 may include receiving sensor data from a plurality of sensors 108, 112, 116, 120 disposed within a plurality of areas of the vehicle 102.

The method 600 may proceed to block 604, wherein the method 600 may include processing the sensor data into metrics associated with a type of measurement. In one embodiment, processing of the sensor data is completed by the neural network 124. The method 600 may proceed to block 606, wherein the method 600 may include analyzing the processed metrics and determining an anxiety level associated with an occupant of the vehicle 102. The method 600 may proceed to block 608, wherein the method 600 may include training the neural network based on the anxiety level and at least one driving event that is correlated with the anxiety level.

It should be apparent from the foregoing description that various exemplary embodiments of the invention may be implemented in hardware. Furthermore, various exemplary embodiments may be implemented as instructions stored on a non-transitory machine-readable storage medium, such as a volatile or non-volatile memory, which may be read and executed by at least one processor to perform the operations described in detail herein. A machine-readable storage medium may include any mechanism for storing information in a form readable by a machine, such as a personal or laptop computer, a server, or other computing device. Thus, a non-transitory machine-readable storage medium excludes transitory signals but may include both volatile and non-volatile memories, including but not limited to read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

It will be appreciated that various implementations of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A computer-implemented method for determining a measurement of anxiety in a vehicle, comprising:
receiving sensor data from a plurality of sensors disposed within a plurality of areas of the vehicle;
processing the sensor data into metrics associated with a type of measurement, wherein processing of the sensor data is completed by a neural network;
analyzing the processed metrics and determining an anxiety level associated with an occupant of the vehicle; and
training the neural network based on the anxiety level and at least one driving event that occurs within a surrounding environment of the vehicle that is correlated with the anxiety level.

2. The computer-implemented method of claim 1, wherein receiving sensor data from the plurality of sensors includes receiving sensor data from a plurality of seat sensors and a plurality of seat belt sensors, wherein the plurality of seat sensors and the plurality of seat belt sensors include pressure sensors and flex sensors that are configured in at least one matrix to sense levels of pressure and biometric data.

3. The computer-implemented method of claim 2, wherein receiving sensor data from the plurality of sensors includes receiving sensor data from a plurality of encoder sensors of an encoder that is included as part of a seat belt retractor mechanism, wherein the plurality of encoder sensors include flex sensors that sense levels of stress placed upon a seat belt of the vehicle.

4. The computer-implemented method of claim 3, wherein receiving sensor data from the plurality of sensors includes receiving sensor data from a plurality of floor sensors, wherein the plurality of floor sensors include pressure sensors that are configured in at least one array to sense levels of force applied to a floor board of the vehicle.

5. The computer-implemented method of claim 4, wherein processing the sensor data into metrics associated with the type of measurement includes filtering sensor data received from the plurality of seat sensors, the plurality of seat belt sensors, the plurality of encoder sensors, and the plurality of floor sensors to remove noise artifacts.

6. The computer-implemented method of claim 5, wherein processing the sensor data into metrics includes communicating noise filtered sensor data that is received for at least one predetermined period of time to the neural network to process a body position metric, wherein the body position metric is processed based on evaluation of the noise filtered sensor data by the neural network to determine metric values that pertain to the body position of the occupant that indicate a particular level of stress and tension of the occupant.

7. The computer-implemented method of claim 6, wherein processing the sensor data into metrics includes communicating the noise filtered sensor data that is received for at least one predetermined period of time to the neural network to process a fidgeting metric, wherein the fidgeting metric is processed based on evaluation of the noise filtered sensor data by the neural network to determine metric values that pertain to a level of fidgeting exhibited by the occupant that indicates a particular level of stress and tension of the occupant.

8. The computer-implemented method of claim 7, wherein processing the sensor data into metrics includes communicating the noise filtered sensor data that are received for at least one predetermined period of time to the neural network to process a ventilation metric, wherein the ventilation metric is processed based on evaluation of the noise filtered sensor data by the neural network to determine metric values that pertain to a ventilation rate exhibited by the occupant that indicates a particular level of stress and tension of the occupant.

9. The computer-implemented method of claim 8, wherein analyzing the processed metrics and determining the anxiety level includes passing the body position metric, the fidgeting metric, and the ventilation metric through at least one pre-trained data classifier, wherein the pre-trained data classifier evaluates the metrics against at least one anxiety level determining model that pertains to a body position, a level of fidgeting, and a ventilation rate of an individual experiencing one or more levels of anxiety.

10. A system for determining a measurement of anxiety in a vehicle, comprising:
a memory storing instructions when executed by a processor cause the processor to:
receive sensor data from a plurality of sensors disposed within a plurality of areas of the vehicle;
process the sensor data into metrics associated with a type of measurement, wherein processing of the sensor data is completed by a neural network;
analyze the processed metrics and determining an anxiety level associated with an occupant of the vehicle; and
train the neural network based on the anxiety level and at least one driving event that occurs within a surrounding environment of the vehicle that is correlated with the anxiety level.

11. The system of claim 10, wherein receiving sensor data from the plurality of sensors includes receiving sensor data from a plurality of seat sensors and a plurality of seat belt sensors, wherein the plurality of seat sensors and the plurality of seat belt sensors include pressure sensors and flex sensors that are configured in at least one matrix to sense levels of pressure and biometric data.

12. The system of claim 11, wherein receiving sensor data from the plurality of sensors includes receiving sensor data from a plurality of encoder sensors of an encoder that is included as part of a seat belt retractor mechanism, wherein the plurality of encoder sensors include flex sensors that sense levels of stress placed upon a seat belt of the vehicle.

13. The system of claim 12, wherein receiving sensor data from the plurality of sensors includes receiving sensor data from a plurality of floor sensors, wherein the plurality of floor sensors include pressure sensors that are configured in at least one array to sense levels of force applied to a floor board of the vehicle.

14. The system of claim 13, wherein processing the sensor data into metrics associated with the type of measurement includes filtering sensor data received from the plurality of seat sensors, the plurality of seat belt sensors, the plurality of encoder sensors, and the plurality of floor sensors to remove noise artifacts.

15. The system of claim 14, wherein processing the sensor data into metrics includes communicating noise filtered sensor data that is received for at least one predetermined period of time to the neural network to process a body position metric, wherein the body position metric is processed based on evaluation of the noise filtered sensor data by the neural network to determine metric values that pertain to the body position of the occupant that indicate a particular level of stress and tension of the occupant.

16. The system of claim 15, wherein processing the sensor data into metrics includes communicating the noise filtered sensor data that is received for at least one predetermined period of time to the neural network to process a fidgeting metric, wherein the fidgeting metric is processed based on evaluation of the noise filtered sensor data by the neural network to determine metric values that pertain to a level of fidgeting exhibited by the occupant that indicates a particular level of stress and tension of the occupant.

17. The system of claim 16, wherein processing the sensor data into metrics includes communicating the noise filtered sensor data that are received for at least one predetermined period of time to the neural network to process a ventilation metric, wherein the ventilation metric is processed based on evaluation of the noise filtered sensor data by the neural network to determine metric values that pertain to a ventilation rate exhibited by the occupant that indicates a particular level of stress and tension of the occupant.

18. The system of claim 17, wherein analyzing the processed metrics and determining the anxiety level includes passing the body position metric, the fidgeting metric, and the ventilation metric through at least one pre-trained data classifier, wherein the pre-trained data classifier evaluates the metrics against at least one anxiety level determining model that pertains to a body position, a level of fidgeting, and a ventilation rate of an individual experiencing one or more levels of anxiety.

19. A non-transitory computer readable storage medium storing instructions that when executed by a computer, which includes a processor perform a method, the method comprising:
receiving sensor data from a plurality of sensors disposed within a plurality of areas of a vehicle;
processing the sensor data into metrics associated with a type of measurement, wherein processing of the sensor data is completed by a neural network;
analyzing the processed metrics and determining an anxiety level associated with an occupant of the vehicle; and
training the neural network based on the anxiety level and at least one driving event that occurs within a surrounding environment of the vehicle that is correlated with the anxiety level.

20. The non-transitory computer readable storage medium of claim 19, wherein analyzing the processed metrics and determining the anxiety level includes passing a body position metric, a fidgeting metric, and a ventilation metric through at least one pre-trained data classifier, wherein the pre-trained data classifier evaluates the metrics against at least one anxiety level determining model that pertains to a body position, a level of fidgeting, and a ventilation rate of an individual experiencing one or more levels of anxiety.

\* \* \* \* \*